(12) United States Patent
Young et al.

(10) Patent No.: US 11,925,800 B2
(45) Date of Patent: Mar. 12, 2024

(54) DEVICE IMPLANTATION USING A CARTRIDGE

(71) Applicant: Neuralink Corp., Fremont, CA (US)

(72) Inventors: Robin E. Young, San Francisco, CA (US); Philip N. Sabes, San Francisco, CA (US)

(73) Assignee: NEURALINK, INC., Fremont, CA (US)

(*) Notice: Subject to any disclaimer, the term of this patent is extended or adjusted under 35 U.S.C. 154(b) by 157 days.

(21) Appl. No.: 17/360,369

(22) Filed: Jun. 28, 2021

(65) Prior Publication Data

US 2021/0346687 A1 Nov. 11, 2021

Related U.S. Application Data

(63) Continuation of application No. 16/569,590, filed on Sep. 12, 2019, now Pat. No. 11,103,695.

(Continued)

(51) Int. Cl.
A61N 1/05 (2006.01)
A61B 17/34 (2006.01)
(Continued)

(52) U.S. Cl.
CPC ........ *A61N 1/0534* (2013.01); *A61B 17/3403* (2013.01); *A61B 17/3468* (2013.01);
(Continued)

(58) Field of Classification Search
CPC ........ A61B 2034/2055; A61B 17/3468; A61B 17/1757; A61B 17/1671; A61B 10/02;
(Continued)

(56) References Cited

U.S. PATENT DOCUMENTS 6,282,437 B1  8/2001 Franck et al.
6,415,187 B1  7/2002 Kuzma et al.
(Continued)

FOREIGN PATENT DOCUMENTS

JP  2004202221 A  7/2004
JP  2004307857 A  11/2004
(Continued)

OTHER PUBLICATIONS

Application No. EP19860686.5, Extended European Search Report, dated Jun. 23, 2022, 11 pages.

(Continued)

*Primary Examiner* — Jon Eric C Morales
(74) *Attorney, Agent, or Firm* — Kilpatrick Townsend & Stockton LLP

(57) ABSTRACT

A system and method for implanting devices into biological tissue (e.g., brain tissue). The system may include a biocompatible probe, an integrated circuit (IC) chip tethered to the probe, a cartridge comprising a temporary attachment surface by which the probe is removably coupled to the cartridge, a needle to reversibly engage with the probe, a robotic arm to hold the needle, and a microprocessor controller. The microprocessor controller may control the robotic arm and the needle to remove the probe from the temporary attachment surface using the needle, pierce the biological tissue with the needle and the probe, withdraw the needle while leaving the probe within the biological tissue, and detach the IC chip from the cartridge, leaving the IC chip with the biological tissue.

20 Claims, 26 Drawing Sheets

Related U.S. Application Data

(60) Provisional application No. 62/731,446, filed on Sep. 14, 2018.

(51) Int. Cl.
| | |
|---|---|
| *A61N 1/36* | (2006.01) |
| *A61B 17/00* | (2006.01) |
| *A61B 90/00* | (2016.01) |
| *A61N 1/372* | (2006.01) |

(52) U.S. Cl.
CPC .............. *A61N 1/36082* (2013.01); *A61B 2017/00026* (2013.01); *A61B 2090/062* (2016.02); *A61N 1/0531* (2013.01); *A61N 1/36064* (2013.01); *A61N 1/37205* (2013.01)

(58) Field of Classification Search
CPC ..... A61B 10/0233; A61B 34/30; A61B 34/70; A61B 34/74; A61M 5/172; A61N 1/0529; A61N 1/0531; A61N 1/0534; A61N 1/0539; A61N 2005/063; A61N 5/0601; A61N 5/0622

See application file for complete search history.

(56) References Cited

U.S. PATENT DOCUMENTS

| | | |
|---|---|---|
| 9,782,229 B2 | 10/2017 | Crawford et al. |
| 11,103,695 B2 | 8/2021 | Young et al. |
| 2003/0114862 A1 | 6/2003 | Chu et al. |
| 2006/0128937 A1 | 6/2006 | Nagasaki et al. |
| 2008/0027317 A1 | 1/2008 | Wood et al. |
| 2009/0299167 A1 | 12/2009 | Seymour |
| 2010/0029148 A1* | 2/2010 | Perlin .................... A61B 5/685 439/884 |
| 2010/0100152 A1 | 4/2010 | Martens et al. |
| 2010/0168727 A1 | 7/2010 | Hancock et al. |
| 2012/0296444 A1 | 11/2012 | Greenberg et al. |
| 2013/0010081 A1 | 1/2013 | Tenney et al. |
| 2013/0274596 A1 | 10/2013 | Azizian et al. |
| 2013/0345718 A1* | 12/2013 | Crawford ............... A61B 5/061 606/130 |
| 2013/0345780 A1 | 12/2013 | Tabada et al. |
| 2014/0213891 A1 | 7/2014 | Gilgunn et al. |
| 2014/0277317 A1 | 9/2014 | Tooker et al. |
| 2014/0288458 A1 | 9/2014 | Yoon et al. |
| 2014/0303703 A1 | 10/2014 | Mercanzini et al. |
| 2015/0018622 A1 | 1/2015 | Tesar et al. |
| 2015/0080740 A1 | 3/2015 | Hao |
| 2016/0278678 A1 | 9/2016 | Valdes et al. |
| 2017/0112354 A1 | 4/2017 | DiCarlo et al. |
| 2017/0112577 A1 | 4/2017 | Bonutti et al. |
| 2017/0172446 A1 | 6/2017 | Kuzum et al. |
| 2018/0014851 A1 | 1/2018 | Hansen et al. |
| 2018/0078767 A1 | 3/2018 | Rapoport et al. |
| 2018/0117309 A1 | 5/2018 | Rapoport et al. |
| 2018/0153408 A1 | 6/2018 | Yao et al. |
| 2018/0235659 A1 | 8/2018 | Oostman, Jr. |
| 2018/0296243 A1* | 10/2018 | Hanson ................ A61N 1/0539 |
| 2020/0085508 A1 | 3/2020 | O'hara et al. |

FOREIGN PATENT DOCUMENTS

| | | |
|---|---|---|
| JP | 2006510416 A | 3/2006 |
| JP | 2008056797 A | 3/2008 |
| JP | 2015505678 A | 2/2015 |
| JP | 2015523102 A | 8/2015 |
| JP | 2015528713 A | 10/2015 |
| WO | 2007089738 A2 | 8/2007 |
| WO | 2016126340 A2 | 8/2016 |
| WO | 2016185525 A1 | 11/2016 |
| WO | 2018102307 A1 | 6/2018 |

OTHER PUBLICATIONS

Application No. JP2021-539469, Office Action, dated Jun. 14, 2022, 11 pages.
Application No. JP2021-539469, Office Action, dated Nov. 8, 2022, 5 pages.
Chan et al., "Implantable Polycrystalline Diamond Neural Probe for in Vivo and in Vitro Physiological Recording", Transducers 2009 : 2009 International Solid-State Sensors, Actuators and Microsystems Conference, Jun. 21, 2009, pp. 1202-1205.
EP19859297.4 , "Extended European Search Report", dated Mar. 25, 2022, 10 pages.
EP19859298.2 , "Extended European Search Report", dated Mar. 30, 2022, 7 pages.
EP19860686.5 , "Partial Supplementary European Search Report", dated Mar. 23, 2022, 13 pages.
Michon et al., "Integration of Silicon-Based Neural Probes and Micro-Drive Arrays for Chronic Recording of Large Populations of Neurons in Behaving Animals", Journal of Neural Engineering, Institute of Physics Publishing, vol. 13, No. 4, Jun. 28, 2016, 11 pages.
U.S. Appl. No. 16/354,059, Network-On-Chip for Neurological Data, filed Mar. 14, 2019, 41 pages.
PCT/US2019/050858, International Preliminary Report on Patentability, dated Jul. 1, 2020, 16 pages.
PCT/US2019/050858, International Search Report and Written Opinion, dated Nov. 19, 2019, 8 pages.
PCT/US2019/050877, International Preliminary Report on Patentability, dated Jul. 16, 2020, 6 pages.
PCT/US2019/050877, International Search Report and Written Opinion, dated Dec. 5, 2019, 12 pages.
PCT/US2019/050886, International Preliminary Report on Patentability, dated Mar. 25, 2021, 12 pages.
PCT/US2019/050886, International Search Report and Written Opinion, dated Feb. 5, 2020, 15 pages.
PCT/US2019/050886, Invitation to Pay Additional Fees and, Where Applicable, Protest Fee, Nov. 13, 2019, 2 pages.
U.S. Appl. No. 16/569,587, Final Office Action, dated Feb. 2, 2021, 20 pages.
U.S. Appl. No. 16/569,587, Non-Final Office Action, dated Jun. 26, 2020, 13 pages.
U.S. Appl. No. 16/569,587, Non-Final Office Action, dated Jun. 16, 2021, 19 pages.
U.S. Appl. No. 16/569,590, Non-Final Office Action, dated Nov. 3, 2020, 18 pages.
U.S. Appl. No. 16/569,590, Notice of Allowance, dated Mar. 30, 2021, 7 pages.
Hanson et al., "The "Sewing Machine" for Minimally Invasive Neural Recording," Available Online at: http://dx.doi.org/10.1101/578542), Mar. 2019, 32 pages.
Musk et al., "An Integrated Brain-Machine Interface Platform with Thousands of Channels," Available Online at: http://dx.doi.org/10.1101/703801, Jul. 2019, 12 pages.
Application No. CA3112875, Notice of Allowance, dated Mar. 27, 2023, 1 page.
Application No. EP19859298.2, Office Action, dated Feb. 20, 2023, 4 pages.
Application No. JP2021-539469, Notice of Allowance, dated Apr. 11, 2023, 2 pages.
Application No. KR10-2021-7010790, Office Action, dated Apr. 7, 2023, 19 pages.
EP19859298.2 , "Office Action", dated Jul. 28, 2023, 6 pages.
JP2021-539470 , "Office Action", dated Jun. 27, 2023, 5 pages.
JP2021-539472 , "Office Action", dated Jul. 25, 2023, 8 pages.

* cited by examiner

DEVICE IMPLANTATION USING A CARTRIDGE

CROSS-REFERENCES TO RELATED APPLICATIONS

This application is a continuation of U.S. patent application Ser. No. 16/569,590 titled "Device Implantation Using a Cartridge" and filed on Sep. 12, 2019, which claims the benefit of priority of U.S. Provisional Application No. 62/731,446 titled "Cartridge for Implantable Devices" and filed on Sep. 14, 2018, which is herein incorporated by reference in its entirety for all purposes.

TECHNICAL FIELD

The present disclosure is generally related to systems and methods for implanting probe devices.

BACKGROUND

Conventional methods to record from and/or stimulate neurological sites are limited by an inability to position and size electrodes such that they are able to precisely record and/or stimulate neurological sites of interest. Additionally, conventional electrodes (and electrode arrays) are unable to achieve reliable and conformal integration with structures in the nervous system. Moreover, conventional electrodes are prone to degradation in the quality of recorded and/or stimulated neurological signals over time.

Without electrodes that are able to record from and/or stimulate neurological sites with precision and over a reliable amount of time, implantable devices for neurological sites that use conventional electrodes have limited use for science and research experiments, neural prostheses (e.g., brain/nerve machine interfaces), and the treatment of neuronal disease (e.g., deep brain stimulation for the treatment of epilepsy).

Conventional approaches to implanting implantable devices having electrodes into neurological tissue suffer from limited depth, limited longevity, limited targeting ability, limitations due to their relatively large size, and limited bandwidth.

BRIEF SUMMARY

In some embodiments, a system for robotically implanting a probe device into biological tissue includes a biocompatible probe, an integrated circuit (IC) chip tethered to the probe, a cartridge comprising a temporary attachment surface by which the probe is removably coupled to the cartridge and a fastener for removably coupling the IC chip to the cartridge, a needle configured to reversibly engage with the probe, a robotic arm configured to hold the needle, a camera, and a microprocessor controller configured to control the robotic arm and the needle using the camera in order to: remove the probe from the temporary attachment surface using the needle, pierce the biological tissue with the needle and the probe, withdraw the needle while leaving the probe within the biological tissue, and detach the IC chip from the cartridge and leave the IC chip with the biological tissue, the IC chip still tethered to the probe.

In some aspects, the probe device assembly may further include multiple probes and IC chips. In some aspects, the fastener comprises one or more of a magnetic attachment or a mechanical attachment.

In some aspects, the temporary attachment surface is formed of one or more of parylene or silicon and the cartridge further comprises an adhesive layer beneath the temporary attachment surface. In some aspects, the system further includes an antenna configured to relay data, electricity, or other signals.

In some aspects, the probe includes an electrode configured to be inserted into biological tissue and a receiving feature mounted on the cartridge for engagement with the needle. In some aspects, the robotic arm is a first robotic arm, and the system further includes a second robotic arm configured to couple with the cartridge.

In some embodiments, a method of implanting a probe device into biological tissue includes (i) providing a cartridge comprising a temporary attachment surface by which the cartridge is removably coupled a biocompatible probe, and a fastener by which the cartridge is removably coupled to an integrated circuit (IC) chip tethered to the probe, (ii) reversibly engaging a needle with the probe, (iii) removing the probe from the temporary attachment surface using the needle, (iv) piercing the biological tissue with the needle and the probe, (v) withdrawing the needle while leaving the probe within the biological tissue, and (vi) detaching the IC chip from the cartridge, leaving the IC chip with the biological tissue, the IC chip still tethered to the probe.

In some aspects, the cartridge has multiple probes and IC chips and the method further includes repeating steps (ii)-(v) for each probe, of the multiple probes. In some aspects, reversibly engaging the needle with the selected receiving feature includes rotating the needle from about 5 degrees to about 180 degrees. In some aspects, the probe is left within the biological tissue at a depth of about one to about three millimeters.

In some embodiments, a cartridge-and-probe-device assembly includes a cartridge comprising a first fastener, a second fastener configured to removably couple the cartridge to a robotic arm, and a temporary attachment surface; an integrated circuit (IC) chip removably coupled to the cartridge via the first fastener; and a biocompatible probe tethered to the IC chip and removably coupled to the temporary attachment surface of the cartridge, wherein the probe includes an electrode configured to be inserted into biological tissue.

In some aspects, the cartridge-and-probe-device assembly further includes a communications port arranged to be exposed outside of the biological tissue and configured to relay data, electricity, or other signals. Alternatively, or additionally, in some aspects, the cartridge-and-probe-device assembly further includes an antenna configured to relay data, electricity, or other signals.

In some aspects, the first fastener includes one or more of a magnetic attachment or a mechanical attachment. In some aspects, the second fastener includes one or more of a magnetic attachment or a mechanical attachment.

In some aspects, the cartridge-and-probe-device assembly further includes multiple probes and IC chips, and a projection edge on the cartridge, configured to mount the multiple probes in a position to be engaged with by a needle for implantation.

In some aspects, cartridge-and-probe-device assembly includes four integrated circuit chips and a storage package structure comprising four chip-compartments, each chip-compartment holding a respective IC chip. In some aspects, the temporary attachment surface is formed of one or more of parylene or silicon; and the cartridge further includes an adhesive layer between the temporary attachment surface and the cartridge. In some aspects, the probe has a thickness in a range of from about 2 micrometers (μm) to about 50 μm.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

DETAILED DESCRIPTION

Figure 1A:
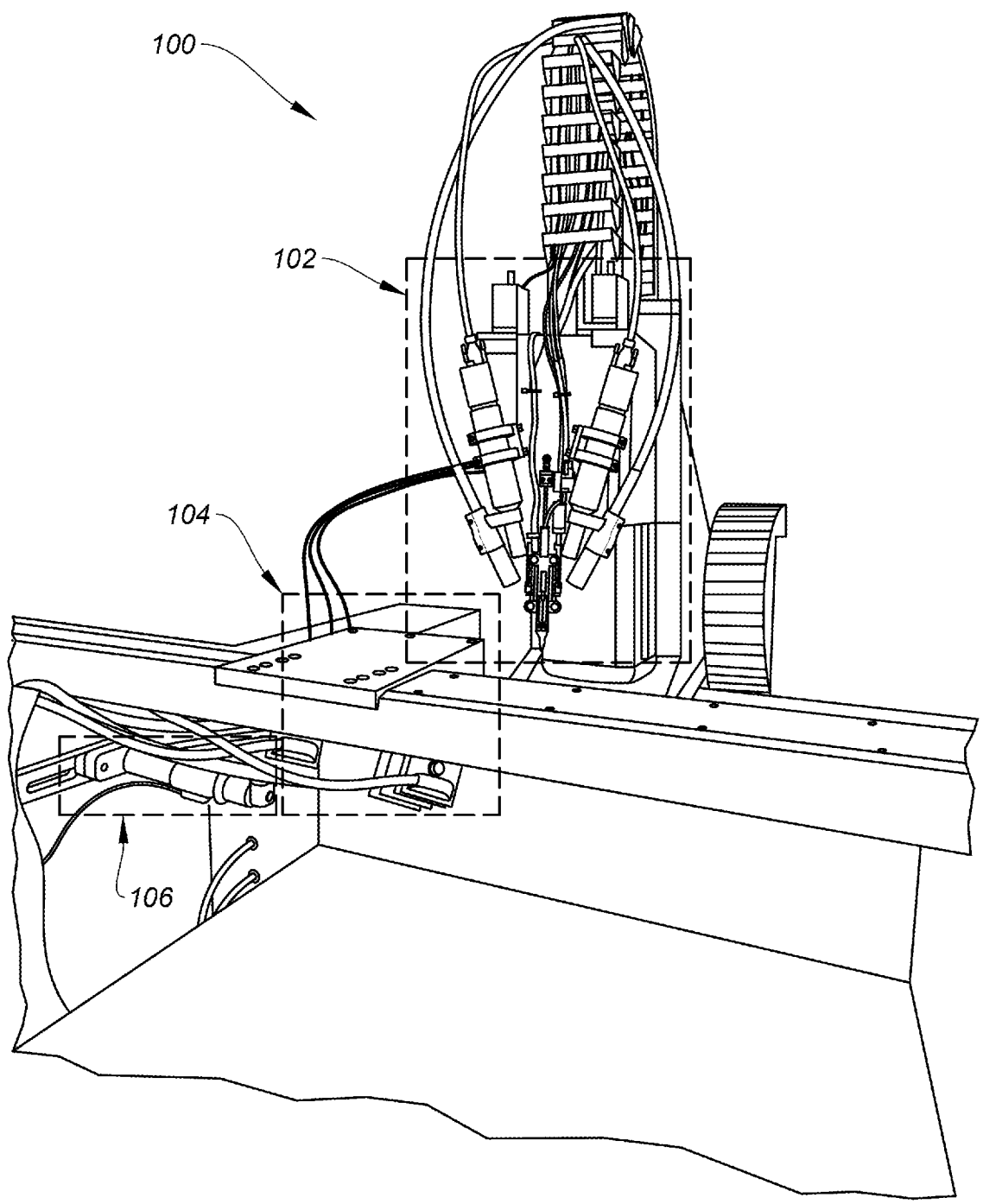
FIGS. 1A and 1B illustrate a system for implanting a device, according to an aspect of the present disclosure.

The present disclosure relates to systems and methods for implanting implantable devices (also referred to herein as "probe device assemblies" or "probe devices") having electrodes that are configured to record and/or stimulate biological tissue. In some embodiments, biological tissue can include neurological tissue (also referred to as "brain tissue"). "Implanting a probe device" may refer to implanting at least a portion of a probe device into tissue. Alternatively, or additionally, implanting a probe device may include disposing a portion of a probe device on, or in proximity to, tissue.

As noted above, conventional approaches to implanting probe devices into neurological tissue suffer from several limitations. Conventional brain implants with electrodes tend to have a limited depth of penetration. Such implants also tend to have a limited longevity or limited functional lifespan, in part because presently existing neural probes are engineered to be stiff enough to penetrate the brain, but evidence suggests that this stiffness along with subsequent mechanical impedance mismatch (i.e., the brain is relatively soft) leads to chronic micro-motion, which in turn leads to scarring and loss of recording and stimulating ability of the electrode. Further, such implants have limited targeting ability. In some prior systems, probe devices are fabricated in rigid two-dimensional (2D) arrays, which cannot be arranged with sufficient flexibility to, for example, be targeted to avoid blood vessels. The limited targeting ability also means that the electrodes as part of conventional structures or 2D arrays cannot can be targeted or placed at dynamically selected or arbitrarily selected positions throughout the brain. Moreover, such implants are limited due to their relatively large size, as compared to the tissue they are stimulating and/or recording. Such large implants can elicit immune and foreign-body responses. Further, such implants have a limited bandwidth in that prior technologies used in such applications can record or modulate only a small fraction of neurons. Further, in some prior systems, probes are implanted using stiffeners, which is a slow process.

Techniques described herein address these issues. Micron-scale probes may be implemented to address the problems associated with insertion of larger probe devices. Specialized systems can manipulate, aim, and implant these small probes, as it would be difficult to impossible to implant such micron-scale probes manually. Further, the probes are coupled to storage package structures which can be disposed on or near the implantation area. The storage package structures may serve to store and protect one or more integrated circuit (IC) chips. The integrated circuit chips may serve to collect and analyze data gathered from the probes. The probes and storage package structure collectively form a probe device assembly. Such a probe device assembly may include thousands of channels, which can be implanted to targeted regions of tissue to obtain high-bandwidth streams of information from the tissue.

The disclosed probe device can include electrodes with improved depth penetration that are able to penetrate approximately below the surface of the cortex. Example electrodes can include those discussed in U.S. Provisional Application No. 62/731,496 entitled "ELECTRODE FABRICATION AND DESIGN", filed Sep. 14, 2018 and hereby incorporated by reference. Additionally, the disclosed probe devices can be implanted using an needle having sufficient stiffness to position and implant the electrodes of the probe device at a desired target. In some embodiments, the needle can disengage with the probe device once the probe device is implanted, leaving only a flexible electrode array in contact with the biological tissue, thereby reducing the chronic micro-motion, scarring, and loss of recording/stimulating effects common to conventional approaches. Additionally, in some embodiments, the probe device can be implanted using the needle and guidance from robotic surgery techniques. The robotic surgery techniques can include a touch-down sensor configured to determine a tie of implantation. Moreover, such robotic surgery techniques can include one or more computer vision techniques useful for targeting procedures that provide improved targeting to avoid blood vessels and the like. Example computer vision techniques are described in U.S. Provisional Application No. 62/731,520 entitled "COMPUTER VISION TECHNIQUES", filed Sep. 14, 2018 and incorporated by reference (hereinafter "the '520 application"). Additionally, the disclosed probe devices can include specially configured, application-specific integrated circuits such as those described in U.S. Provisional Application No. 62/644,217 entitled "NETWORK-ON-CHIP FOR NEUROLOGICAL DATA", filed on Mar. 16, 2018, and related Non-Provisional application Ser. No. 16/354,059, filed Mar. 14, 2019, which are hereby incorporated by reference.

Other approaches to implementing a needle for implanting a probe device can be found in PCT/US2015/066879 entitled "METHODS, COMPOSITIONS, AND SYSTEMS FOR DEVICE IMPLANTATION" filed on Dec. 18, 2015, and PCT/US2017/063492 entitled "MICRONEEDLE FABRICATION AND DEVICE IMPLANTATION" filed on Nov. 28, 2017, the contents of which are hereby incorporated by reference.

As should be appreciated from the present disclosure and the disclosures referenced above, a probe device that overcomes the limitations of conventional approaches to implanting probe devices will have extremely small and fine electrodes. In some embodiments, an array of such electrodes will be connected as part of an overall probe device, where the electrodes are connected to each other and connected to a central module of the implant with similarly small and fine filament-like connections. In some such aspects, the probe device can be considered like a mesh, with electrodes extending out as terminal points of the implant, arranged and configured to send and receive signals. In some aspects, the probe device with such a plurality of terminal electrodes covering the brain can be understood as akin to a multiplexer, having multiple inputs and directing signal individually or in aggregate through an output signal. Of course, the probe device can also be configured to deliver signals through the plurality of electrodes, effectively operating in the opposite direction of current or data.

As should be further appreciated, the probe device assembly may include a storage package structure holding circuitry, which can have variable shapes and sizes, and can be configured to remain in vivo within a subject along with the probe device following surgery. The storage package structure can be, for example, disposed within a portion of the skull of an animal that has been shaved or carved out to accommodate the storage package structure. The probe device assembly can further include a communications relay to transmit and receive signals to and from the probe device. In some aspects, the probe device assembly can further include a port that extends through the skull and is exposed though the skin of the subject, providing an external access point outside of the biological tissue, where the port can relay data, electricity, or other signals. In other aspects, the probe device assembly can further include a wireless communications port, including an antenna configured to transmit on radio frequencies, Wi-Fi frequencies, or the like, in order to relay data, electricity (e.g. for charging the probe device), or other signals.

Many of the details, dimensions, angles and other features shown in the Figures are merely illustrative of particular embodiments. Accordingly, other embodiments can include other details, dimensions, angles and features without departing from the spirit or scope of the present invention. Various embodiments of the present technology can also include structures other than those shown in the Figures and are expressly not limited to the structures shown in the Figures. Moreover, the various elements and features shown in the Figures may not be drawn to scale. In the Figures, identical reference numbers identify identical or at least generally similar elements.

As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as shown in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below, depending on the context of its use. The device may be otherwise oriented (rotated 90 degrees or at other orientations) and the spatially relative descriptors used herein are interpreted accordingly.

Although the terms "first", "second", etc. may be used herein to describe various elements, components, regions, layers and/or sections, it should be understood that they should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As used herein, the terms "and/or" and "at least one of" include any and all combinations of one or more of the associated listed items.

As used herein, the terms "approximately" and "about" are used to provide flexibility to a numerical range endpoint by providing that a given value may be within a functional range greater than or less than the given value. As used herein, unless otherwise specified, the given value modified by approximately or about is modified by ±10%.

System Overview

Figure 1B:
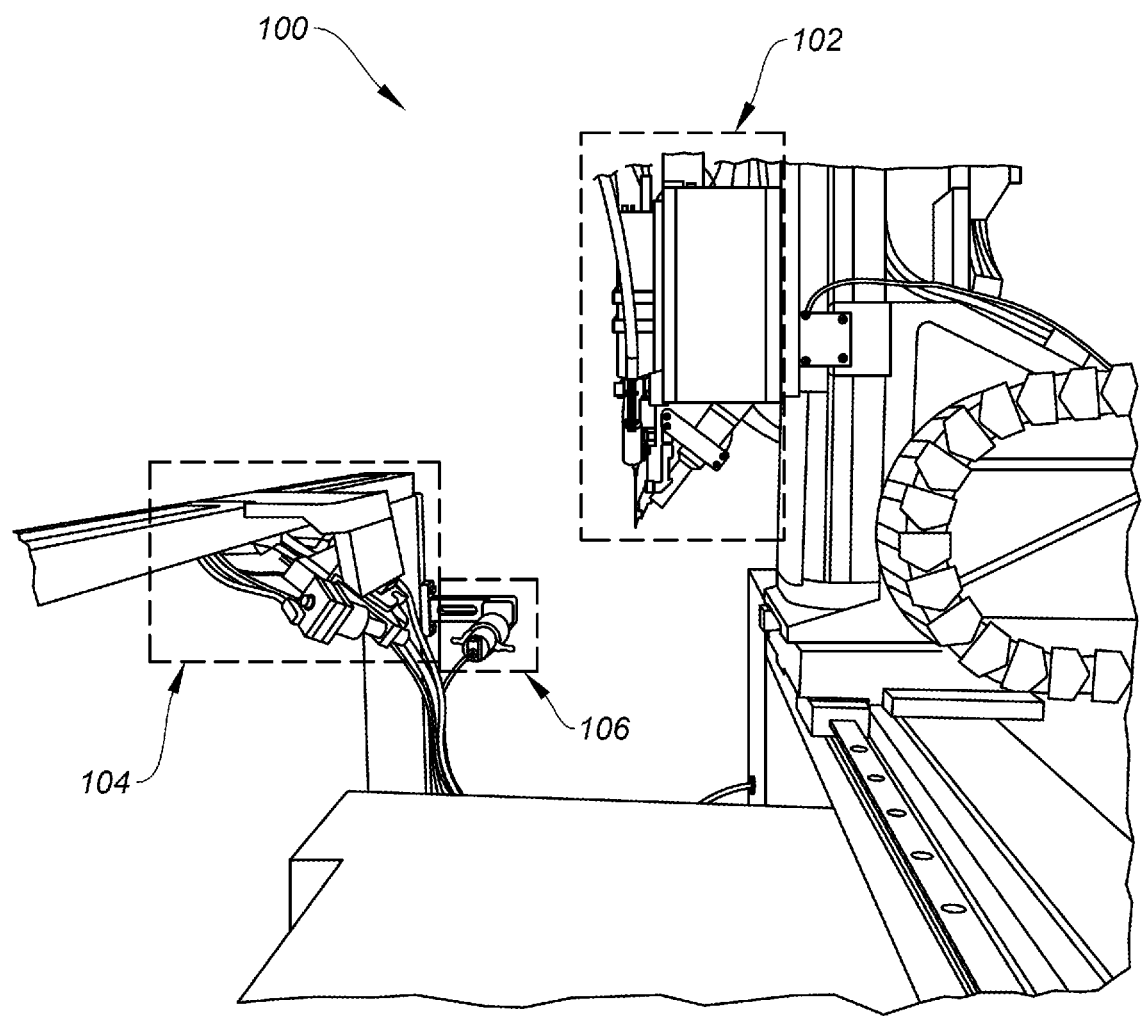

FIGS. 1A and 1B illustrate a system 100 for implanting a device according to some embodiments. FIG. 1A is a front view of system 100. FIG. 1B is a side view of the system 100. System 100 includes an inserter head 102, a probe device stage 104, and a cleaner 106.

The inserter head 102 includes components for implanting a probe device in biological tissue, and is described in further detail below with respect to FIG. 2. The probe device stage 104 includes components for aligning a probe device for implantation. Probe device stage 104 is described in further detail below with respect to FIG. 3.

The cleaner 106 may include functionality for cleaning components of system 100. Cleaner 106 may, for example, be an ultrasonic cleaner. Cleaner 106 may be configured to sterilize a needle after insertion and retraction of the needle. Cleaner 106 may facilitate rapidly and automatically sterilizing the needle, which in turn facilitates successful and rapid insertion of probe devices.

Figure 2:
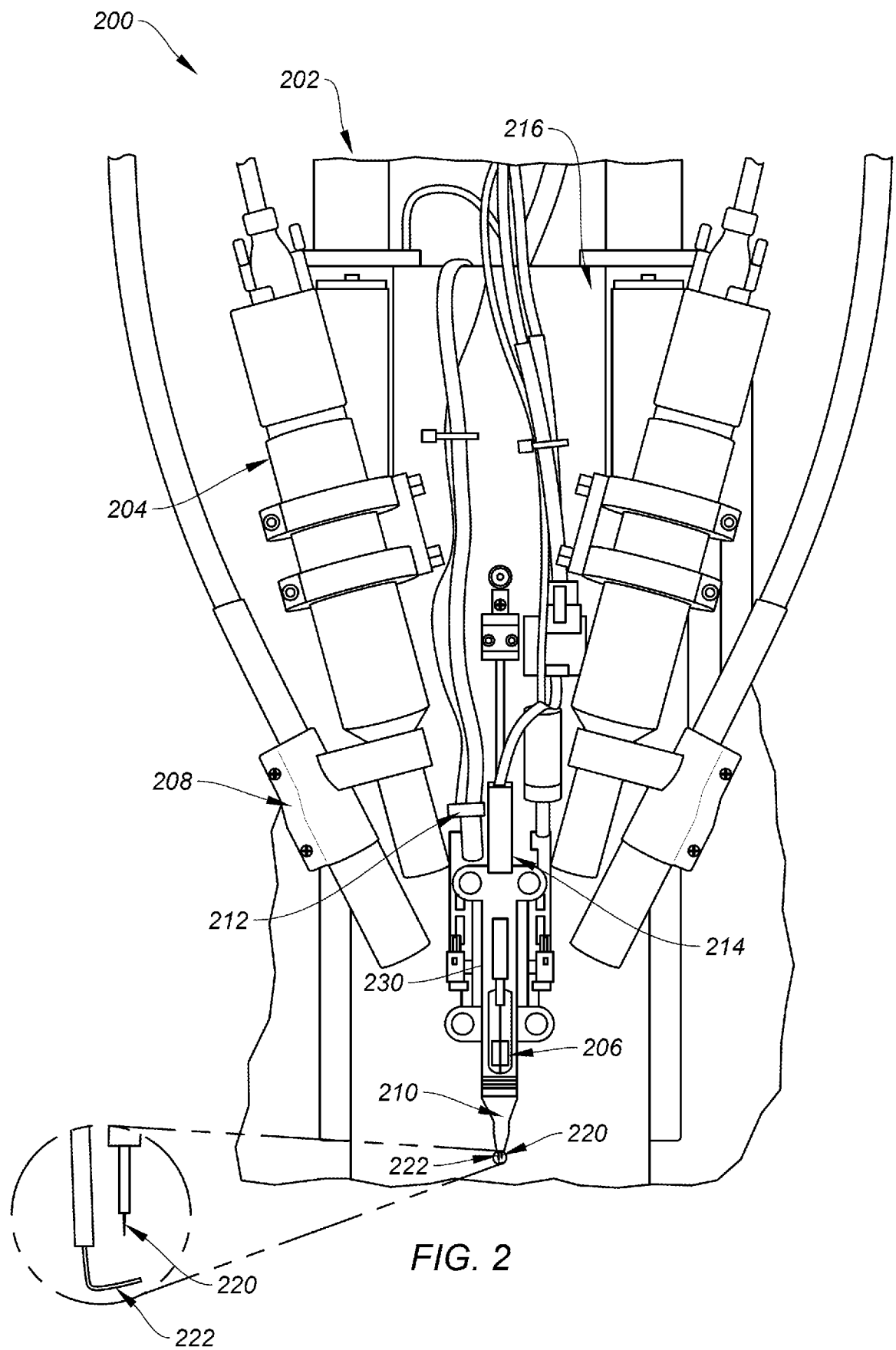
FIG. 2 illustrates an inserter head including a needle for inserting a probe, according to an aspect of the present disclosure.

FIG. 2 illustrates an inserter head 200 according to some embodiments. Inserter head 200 includes elements for implanting a portion of a probe device into biological tissue. Inserter head 200 may include targeting camera actuators 202, targeting cameras 204, an insertion camera 206, light pipe assemblies 208, a needle assembly 210 configured to hold a needle 220, a pincher actuator 212, a needle actuator 214, and an insertion arm 230.

Needle assembly 210 may include a needle 220 and pincher 222 movably attached to a substrate disposed on insertion arm 230. Needle assembly 210 may be small (e.g. on the millimeter scale). Needle assembly 210 may be configured to be quickly and easily installed or replaced on insertion arm 230.

Needle 220 may be configured for inserting portions of probe devices into tissue. Needle 220 may be composed of one or more materials such as tungsten, rhenium, iridium, or carbon. As a specific example, needle 220 may be composed of a tungsten-rhenium wire. Needle 220 may be milled from and/or electrochemically etched to achieve a small diameter, e.g., 24 µm, and/or 20-50 µm. In some embodiments, needle 220 may be less than 20 µm, or more than 50 am in diameter. Needle 220 may include a cannula to facilitate implantation of probe devices.

Pincher 222 may be configured to guide probe devices for insertion. Pincher 222 may be a wire composed of material such as tungsten. Pincher 222 may be bent (e.g., at an approximately 90 degree angle). Pincher 222 may be approximately 50 µm in diameter (e.g., of comparable scale to needle 220). Pincher 222 may serve to support probe devices in transport, as well as to ensure that probe devices, or portions thereof, are inserted along a path of needle 220. Pincher 220 may be configured to extend and retract in operation. Pincher 220 may be configured to rotate to pinch a probe device, e.g., against needle 220. Needle 220 and pincher 222 are not shown to scale.

In some embodiments, needle assembly 210 may include a "touch-down" sensor (not pictured). The touch-down sensor may be configured to deploy from the needle assembly 210 and sense the presence of the biological tissue along a vertical axis. In some aspects, the touch-down sensor can include a force sensor. In other aspects, the touch-down sensor can include capacitor-based electrical sensor. The touch-down sensor can be deployed from needle assembly 210 and then retracted into needle assembly 210 when the presence of the biological tissue is detected. The touch-down sensor can be beneficial in surgical techniques that are performed on live biological tissue, such as the brain, which can pulse and/or move in the vertical direction during surgery.

Needle assembly 210 may be coupled to insertion arm 230 (also referred to herein as a robotic arm). Insertion arm 230 may be a structure for effecting motion of the needle assembly 210. Insertion arm 230 may include, or be coupled to, a motor for driving motion. The motor may, for example, be a linear motor configured for variable insertion speeds and rapid retraction acceleration. Insertion arm 230 may be coupled to a microprocessor controller and/or computing device for sending instructions to insertion arm 230 for controlling motion of needle assembly 210.

Figure 3:
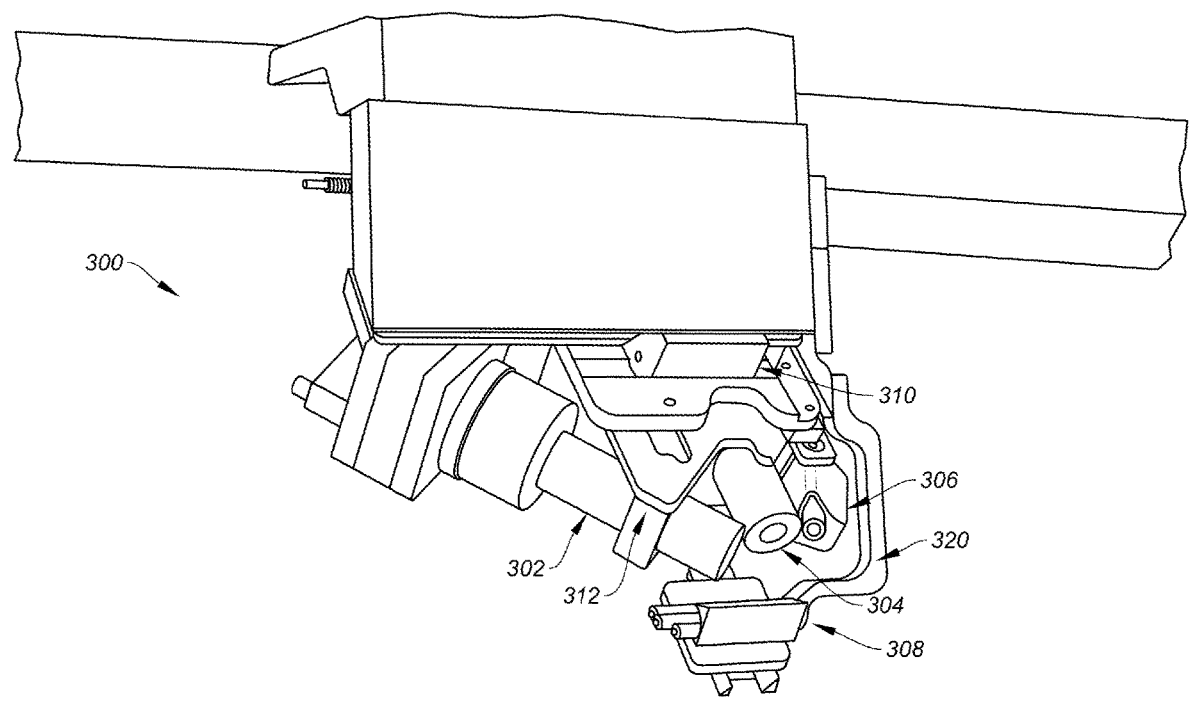
FIG. 3 illustrates a probe device stage including a cartridge-pillbox assembly, according to an aspect of the present disclosure.

The microprocessor controller may be configured to control motion of one or more of the insertion arm 230, the cartridge arm 320 of FIG. 3, and/or the visualization components (e.g., targeting camera(s) 204, insertion camera(s) 206, front camera stack 304, side camera stack 302, and/or light pipe assemblies 208 and 306). The microprocessor controller may receive, as input, visualization information received from the visualization components. The visualization information may provide information for the microprocessor controller to use to determine direction and/or speed information for controlling the insertion arm 230 and/or cartridge arm 320. The microprocessor controller may analyze the visualization information to determine motion instructions. The microprocessor controller may transmit motion instructions to the insertion arm 230 and/or cartridge arm 320 to control motion thereof. The microprocessor controller may further determine and transmit fine motion instructions to the pincher actuator 212 and needle actuator 214 in a similar fashion.

Insertion arm 230 may include pincher actuator 212 for causing motion of the pincher 222 and needle actuator 214 for causing motion of the needle 220. In some embodiments, motion of the insertion arm 230 as a whole corresponds to relatively large-scale motion, while motion of pincher actuator 212 and needle actuator 214 corresponds to fine motions. Pincher actuator 212 and needle actuator 214 may be moved using the same, or different, microprocessor controllers, computing devices, and motors as insertion arm 230.

Motion of inserter head 200 may be controlled using one or more visualization devices, which may include cameras (e.g., targeting cameras 204 and/or insertion camera 206). Images obtained by the visualization devices may be used to determine motion of insertion arm 230.

Targeting cameras 204 and insertion camera 206 may be cameras for capturing a video feed and/or still images. Inserter head 200 may include one or more targeting cameras 204 and/or insertion cameras 206. Targeting cameras 204 may be used to capture images of the area in which an implant is being inserted, which can be used to control the insertion process. Multiple targeting cameras 204 may be used to achieve a stereoscopic effect. In the example shown in FIG. 2, two targeting cameras 204 are provided. Alternatively, one, three, four, or more targeting cameras 204 may be used. Insertion camera 206 may be configured to focus on needle 220 during implantation. Similarly, one or more insertion cameras 206 may be implemented.

Targeting camera actuators 202 may control motion of targeting cameras 204. Targeting camera actuators 202 may include mechanical components for moving targeting cameras 204, coupled to a microprocessor controller, which may be the same as, or different from, the microprocessor controller that controls motion of insertion arm 230 and/or components thereof. A targeting camera actuator 202 may be coupled to each targeting camera 204. In FIG. 2, two targeting camera actuators 202 are shown, one coupled to each targeting camera 204.

Light pipe assemblies 208 may include functionality for illuminating the area in which the implant is to be inserted. In some embodiments, the light pipe assemblies 208 may be configured to generate targeted wavelengths of light to facilitate computer vision techniques, as described in the '520 application.

FIG. 3 illustrates a probe device stage 300 according to some embodiments. Probe device stage 300 includes elements for guiding probe devices for implantation. Probe device stage 300 may include a side camera stack 302, a front camera stack 304, light pipe assemblies 306, a cartridge-pillbox assembly 308, a camera pan actuation assembly 310, a camera focus actuation assembly 312, and a cartridge arm 320.

Cartridge-pillbox assembly 308 (also be referred to herein as a "cartridge-and-probe-device assembly") includes a cartridge for guiding implantation of one or more probe device assemblies (also referred to as probe devices). The probe device assemblies may include one or more probes coupled to a storage package structure or "pillbox." The storage package structure may hold electronics such as one or more circuits which are protected (e.g., hermetically sealed) by the storage package structure. The cartridge may be removably attached to the probes and/or storage package structure. "Removably attached" or "removably coupled" may refer to components that are attached and can be detached relatively easily. For example, magnetically attached components, and components snapped together via mechanical attachments that are loosened with a simple motion, are removably attached. Cartridge-pillbox assembly 308, cartridges, and probe device assemblies are described in detail below with respect to FIGS. 4-7.

Cartridge arm 320 (also referred to as a robotic arm) may be removably coupled to cartridge-pillbox assembly 308. Cartridge arm 320 may be a structure for effecting motion of the cartridge-pillbox assembly 308. Cartridge arm 320 may include, or be coupled to, a motor for driving motion of cartridge arm 320. Cartridge arm 320 may be coupled to a microprocessor controller and/or computing device for sending instructions to cartridge arm 320 for controlling motion of cartridge-pillbox assembly 308, as described above with respect to FIG. 2.

Alternatively, or additionally, in some embodiments, cartridge-pillbox assembly 308 may be detached from the rest of system 100. For example, one or more cartridge-pillbox assemblies 308 may be placed in proximity to inserter head 200 of FIG. 2, without attaching cartridge-pillbox assembly 308 to a cartridge arm 320. Insertion arm 230 may move to engage with components of a fixed cartridge-pillbox assembly in this case.

If cartridge-pillbox assembly 308 is attached to cartridge arm 320, motion of cartridge arm 320 and attached cartridge-pillbox assembly 308 may be controlled using one or more visualization devices, which may include cameras (e.g., camera stacks 302 and 304). Images obtained by the visualization devices may be used by the microprocessor controller to control motion of cartridge arm 320.

Camera stacks 302 and 304 may include cameras for capturing a video feed and/or still images. Front camera stack 304 and side camera stack 302 may be oriented with respect to one another to obtain front and side views of the target implantation region. Camera stacks 302 and 304 may be used to capture images of the area in which an implant is being inserted, which can be used to control the insertion process. In some embodiments, camera stacks 302 and 304 are fixedly coupled to one another (e.g., with a bracket or clamp). In the example shown in FIG. 3, two camera stacks 302 and 304 are provided. Alternatively, one, three, four, or more camera stacks may be used.

Light pipe assemblies 306 may include functionality for illuminating the area in which the implant is to be inserted. In some embodiments, the light pipe assemblies 208 may be configured to generate targeted wavelengths of light for use in computer vision techniques.

Camera pan actuation assembly 310 may include mechanical elements for causing panning motion of camera stacks 302 and 304. Camera pan actuator assembly 310 may swivel the cameras horizontally from a fixed position. In some embodiments, camera pan actuator assembly 310 may move the camera stacks 302 and 304 together so both camera stacks 302 and 304 pan in a same direction while maintaining a same orientation with respect to one another. Camera pan actuator assembly 310 may be communicatively coupled to a microprocessor controller and computing device for sending instructions to camera pan actuator assembly 310 to control motion thereof.

Camera focus actuation assembly 312 may include mechanical elements for causing focusing motion of the camera stacks 302 and 304. Camera focus actuator assembly 312 may adjust the distance between the camera stacks 302 and 304 and a target area. Camera focus actuator assembly 312 may move the camera stacks 302 and 304 together so both camera stacks 302 and 304 focus in a same direction while maintaining a same orientation with respect to one another. Alternatively, or additionally, camera focus actuator assembly 312 may include separate fine focus elements for controlling fine focus of side camera stack 302 and front camera stack 304 separately. Camera focus actuator assembly 312 may be communicatively coupled to a microprocessor controller and computing device for sending instructions to camera focus actuator assembly 312 to control motion thereof. Camera pan actuator assembly 310 and camera focus actuator assembly 312 may be controlled by the same, or different, microprocessor controllers and computing devices.

Probe Device Assembly

Figure 4:
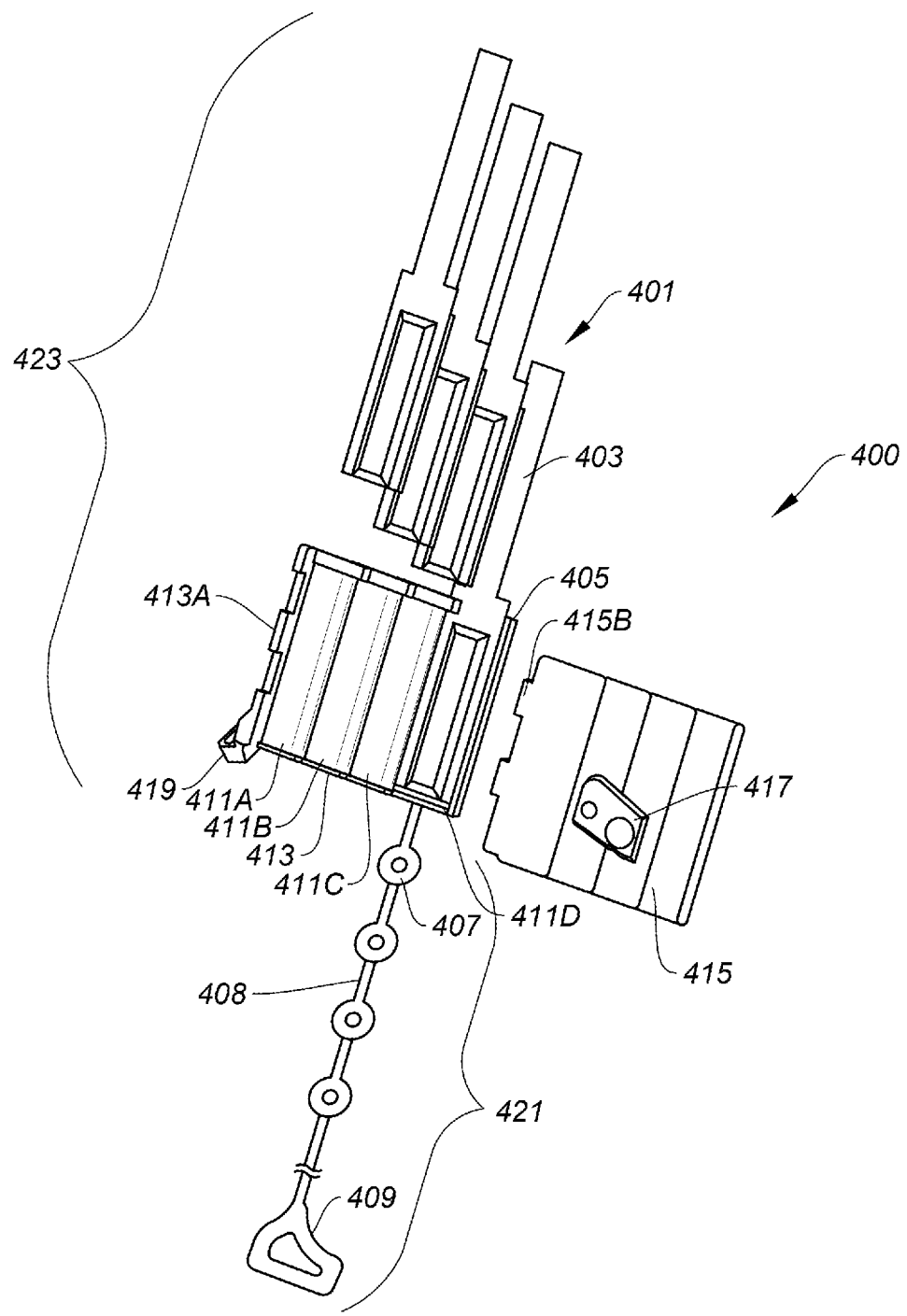
FIG. 4 illustrates a probe device assembly, according to an aspect of the present disclosure.
Figure 5:
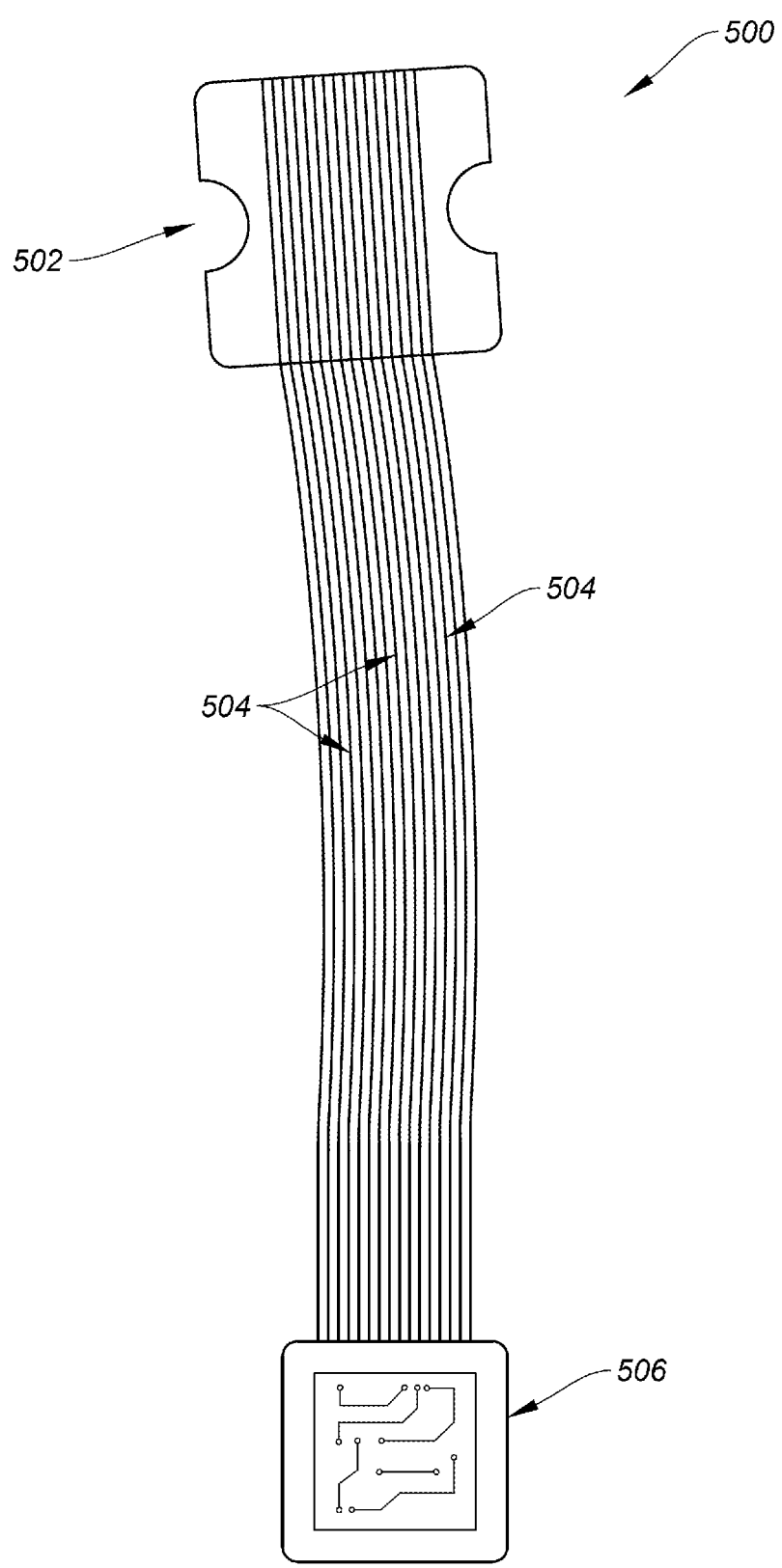
FIG. 5 illustrates a probe device assembly, according to another aspect of the present disclosure.

The implantable devices to be implanted using the system 100 of FIG. 1 may include implantable portions, or probes, which are biocompatible and micron-scale, so as to have a low profile in the insertion regions and interface with biological tissue in a minimally invasive manner. One or more such probes may be communicatively coupled to a storage package structure storing one or more integrated circuit chips to form a probe device assembly. FIGS. 4 and 5 illustrate two examples of such probe device assemblies.

FIG. 4 illustrates a probe device assembly 400, depicted in an exploded view, according to some embodiments. Probe device assembly 400 may include one or more probes 421 communicatively coupled to a storage package structure 423.

Probe 421 is a device for implantation into biological tissue. Probe 421 may be a biocompatible probe, e.g., composed of biocompatible material such as polyimide or other polymetric material. Probe 421 may include a wire 408 for insertion into the biological tissue, one or more electrodes 407 disposed on wire 408, and a receiving feature 409.

Wire 408 may be a thin piece of polymer including one or more biocompatible thin film materials. Wire 408 may include conductive material to transmit information. For example, wire 408 may include a gold thin film trace. In some embodiments, the gold thin film trace is encased in polyimide substrate. For example, a thin film layer of polyimide is deposited, then a gold thin film layer is deposited, then another thin film layer of polyimide is deposited, such that the gold thin film layer is sandwiched between the polyimide layers. In some embodiments, wire 408 may include up to three layers of insulation and two layers of conductor. Although a single probe 421 is illustrated in FIG. 4, as one skilled in the art would recognize, multiple probes 421 may be included in the probe device assembly 400.

Electrodes 407 are small pieces of electrically conductive materials. Electrodes 407 may be configured for recording and/or stimulation of biological tissue (e.g., stimulating neurons in the brain and recording neural spikes from the brain). Alternatively, or additionally, wire 408 may be dispersed with other conduits for conducting information such as a wave guide or microfluidic channel. In some embodiments, the electrodes 407 (or other conduits) are spaced by approximately 50 µm, 75 µm, and/or between 25-100 µm. Each probe 421 may include approximately 32 electrodes 407 and/or between 1-100 electrodes or 25-75 electrodes 407. Electrodes 407 may be configured to be inserted into biological tissue (e.g., biocompatible and/or sized to be inserted into biological tissue).

One end of wire 408 may terminate in a receiving feature 409. Receiving feature 409 may be a feature for receiving a needle and/or engagement feature. Examples of receiving features 409 include a loop, hook, or clamp. For example, wire 408 may include a (16×50) µm² loop to receive an engagement feature of a micron-scale needle.

FIG. 4 is a schematic representation of probe device assembly 400 and not to scale. Probe 421 may be significantly smaller than storage package structure 423. Probe 421 may be dimensioned on the micron-scale (e.g., probe 421 has a size best measured in micrometers (μm)). For example, probe 421 may have a thickness in a range of from about 2 micrometers (μm) to about 50 μm. As a specific example, the thickness of probe 421 may be in the range of about 4 μm to 6 μm, which is a suitable dimension for minimally invasive implantation into brain tissue. As another specific example, the thickness of probe 421 may be in the range of about 15 μm to 30 μm. In various other aspects, probe 421 can have a width that is less than 2 μm or greater than 50 μm.

In some embodiments, probe 421 may have a length from the receiving feature 409 to the chip-compartment portion 413 that is in the range of from about 100 μm to 50 mm. As a specific example, the length of probe 421 is approximately 20 millimeters (mm). In various other aspects, probe 421 can have a length that is less than 100 μm or greater than 50 mm. While only four (4) electrodes 407 are represented in the partial illustration of probe 421 shown in FIG. 4, it is understood that a plurality of electrodes can be present along the length of probe 421, ranging up to as many as 200 electrodes, or in other aspects, greater than 200 electrodes. As a specific example, probe 421 may include 32 electrodes.

In some embodiments, probe device assembly 400 may include an antenna 403. Antenna 403 may include functionality for wirelessly transmitting and receiving data. Alternatively, or additionally, a subset of probe device assemblies 400 may include antenna 403. For example, a first probe device assembly may include an antenna, and wired connections to a set of additional probe device assemblies 400, such that the first probe device assembly 400 externally transmits data gathered from the additional probe device assemblies 400.

Probe device assembly 400 may further include one or more chips 405 (also referred to herein as an integrated circuit chip). Chip 405 may be a specially configured integrated circuit (IC) or electrical chip 405. Chip 405 may be communicatively coupled to the electrodes 407 via wire 408. Chip 405 may be connected to at least one antenna 403 configured to wirelessly transmit and receive data and information to and from the chip 405. Accordingly, the chip 405 can be configured to be in electronic communication, informational communication, and/or operational communication with both antenna 403 and electrodes 407.

Chips 405 can be disposed within a storage package structure 423. Storage package structure 423 may also be referred to herein to as an electronics storage package structure or a pillbox. Storage package structure 423 may protect chips 405 and other electronics from moisture and other impurities associated with proximity to biological tissue.

Storage package structure 423 may include one or more chip-compartments 411A, 411B, 411C, and 411D in which chips 405 can be disposed (collectively, chip-compartment portion 413). In some embodiments, a plurality of chips 405 can fit within the chip-compartment portion 413 of the pillbox. As illustrated in FIG. 4, chip-compartment portion 413 includes four chip-compartments (411A-411D). Each chip-compartment (411A-411D) may hold a corresponding chip 405. Accordingly, in some embodiments, a storage package structure 423 includes four chips 405. Alternatively, or additionally, chip-compartments may be provided for any suitable number of chips, such as one, two, three, five, or ten chips.

The chip-compartment portion 413 can include pillbox component engagement features 413A. A second portion, a cover 415 of storage package structure 423, can be configured to engage with the chip-compartment portion 413 via pillbox component engagement features 415B. Chip-compartment portion 413 of the pillbox may be mechanically connected to cover 415 of storage package structure 423 by way of the pillbox component engagement features 413A and 415B. Alternatively, or additionally, an adhesive can be applied to affix cover 415 to chip-compartment portion 413. The adhesive may, for example, be epoxy or any other suitable materials. In some embodiments, the adhesive is an electrically isolated, thermally insulated material.

In some embodiments, at least one of the chip-compartment portion 413 or the cover 415 of storage package structure 423 can include a pillbox-head plate engagement feature 419 that is configured to engage the pillbox with a head plate (e.g., head plate 901, shown and described below with respect to FIG. 9B).

In some embodiments, probe device assembly 400 may include a pillbox-cartridge engagement feature 417 that is located on an outer surface of storage package structure 423. The pillbox-cartridge engagement feature 417 may include magnets and/or mechanical alignment elements configured to removably couple probe device assembly 400 to a cartridge (e.g., the cartridge depicted in FIGS. 6A-7), such that probe device assembly 400 can engage and disengage from the cartridge. In some embodiments, magnets can engage the pillbox and cartridge on a first axis (e.g., vertically), while alignment elements can mechanically secure the pillbox and cartridge such that they do not move along a second axis (e.g., horizontally).

In some embodiments, storage package structure 423 can differ in size, orientation, and shape based on the chip and/or antenna used. In some embodiments, storage package structure 423 can differ in size, orientation, and shape based on the curvature of the brain. In some embodiments, the location of pillbox-head plate engagement feature 419 can vary based on whether the pillbox is configured for implantation on the right or left hemisphere of the brain. For example, pillbox-head plate engagement features 419 can be positioned to mechanically engage (e.g., clip-in) to the head plate along the outer perimeter of the biological tissue.

In some embodiments, storage package structure 423, including chip 405 and/or antenna 403, can form a collection of components of the probe device assembly that are configured to be positioned at or above the surface of the biological tissue when the probe is implanted in biological tissue.

In some implementations of the systems and methods of the present disclosure, the shape and configuration of probe device assemblies 400 is the same for both the left and right sides of a brain. In other implementations, two separate types of probe device assemblies 400 (often mirrored in shape and configuration) are used for the left and right sides of a brain, respectively.

In some embodiments, a portion of probe device assembly 400 may extend beyond the skull and skin of a subject. In some cases, a single probe device assembly 400, or a condensed set of probe device assemblies 400, may be implanted so as to protrude from the skull and skin in a specific area (e.g., so as to appear similar a Mohawk hairstyle). This may be suitable for use in small animals such as a rat, where the space between the brain and the skull is relatively small. Alternatively, smaller probe devices may be placed under the skin of a subject, as described below with respect to FIG. 5. This configuration may be preferred for larger animals such as humans or non-human primates.

FIG. 5 illustrates another embodiment of a probe device assembly 500. Probe device assembly 500 includes a storage package structure 506 coupled to a plurality of probes 504.

Probes 504 may be substantially similar to probes 421, described above with respect to FIG. 4. Probes 504 may include a wire (similar to wire 408 of FIG. 4), one or more electrodes (similar to electrodes 407 of FIG. 4), and receiving features (similar to receiving feature 409 of FIG. 4). The electrodes and receiving features, although not visible at the scale pictured in FIG. 5, are shown in FIG. 4.

Each probe device assembly 500 may include from about 1 to 200 probes 504 or more than 200 probes 504. In particular, a probe device assembly may include 48 or 96 probes 504.

Proximate to the receiving feature, a portion of probe 504 may be deposited on a temporary attachment surface 502 that holds probe 504 in place until probe 504 is peeled off of temporary attachment surface 502 (e.g., using the needle 220 and needle actuator 214 shown above in FIG. 2). Suitable materials for the temporary attachment surface 502 include parylene (e.g., parylene C) and silicon. Temporary attachment surface 502 may be fused to a cartridge as described below with respect to FIGS. 6A-7.

A second end of each probe 504 may terminate at a chip in storage package structure 506. Storage package structure 506 may enclose and hermetically seal one or more chips therein. The probes 504 may be bonded or tethered to contacts on the chip. Probes 504, of a given probe device assembly 500, may be connected to a single circuit board. Alternatively, probes 504 may be connected to multiple circuit boards (e.g., one probe 504 per circuit board). In various embodiments, the storage package structure 506 can have a size that is about from 50 μm to 100 mm wide, 50 μm to 100 mm wide in length, and 50 μm to 100 mm wide deep. Probe device assembly 500 may be, relative to the embodiment as shown in FIG. 4, about three to four times more compact in volume. The density of the electronics within the electronics storage package structure of this implementation may be about ten times as dense as the embodiment as shown in FIG. 4.

Figure 7:
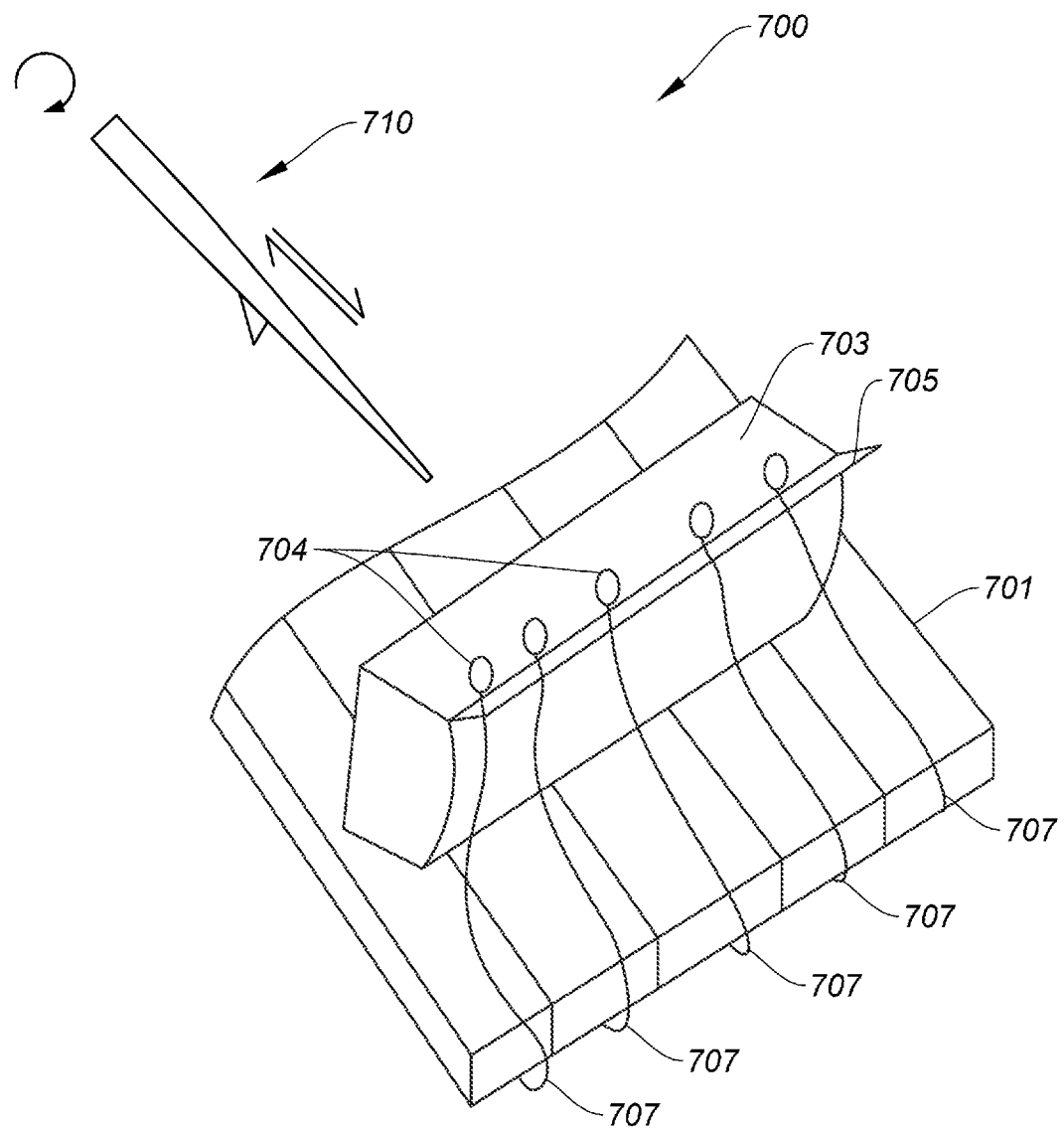
FIG. 7 illustrates a cartridge-pillbox assembly, according to an aspect of the present disclosure.
Figure 11:
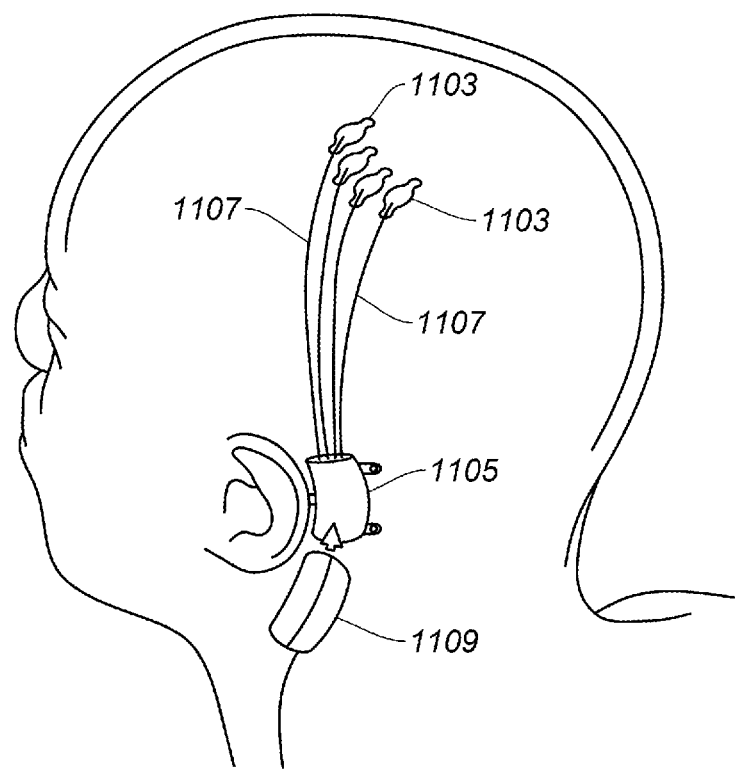
FIG. 11 illustrates implanted probe device assemblies, according to another aspect of the present disclosure.

Storage package structure 506 can have a rectangular shape (e.g., as illustrated in FIG. 7), but can also have an oblong, spherical, circular, triangular, hexagonal, generally convex, generally concave, or other such shape. As shown in FIG. 11, storage package structure may have a generally elliptical shape. Probes 504 may extend out of the storage package structure 506 for implantation.

In some embodiments, each probe device assembly 500 can be connected via a cable (e.g., flexible cable or wire) to a connector port. The connector port may extend outside of the body and skin of a subject. In some cases, the connector port is the only portion that is exposed outside of the body or skin. Alternatively, or additionally, the total number of probe device assemblies 500 implanted in a subject, and the related electrodes inserted into the neurological tissue, will be connected to a single communications module having a direct (wired) port or wireless transmission structure. In other words, the chip, container, and array are all completely under the skin, and moreover largely on bone (e.g. placed into a formed recess in the skull) when implanted, with only (in some embodiments) a port breaking the skin to provide for external access to the probe device assembly once implanted. In alternative embodiments, two communications modules could be used (e.g., one for each hemisphere of the brain). In other alternative embodiments, two separate modules implanted in the subject could be used, one for communications and one for power (e.g., for charging the implanted device). Alternatively, or additionally, one or more probe device assemblies may include an antenna for wireless communication. One configuration of multiple probe device assemblies and communication elements is illustrated and described in detail below with respect to FIG. 11.

Cartridge

Figure 6A:
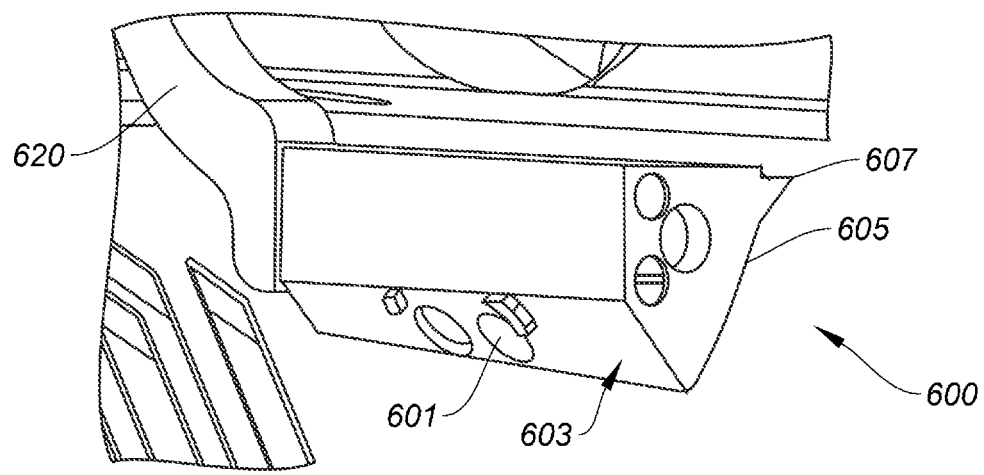
FIGS. 6A and 6B illustrate a cartridge, according to an aspect of the present disclosure.
Figure 6B:
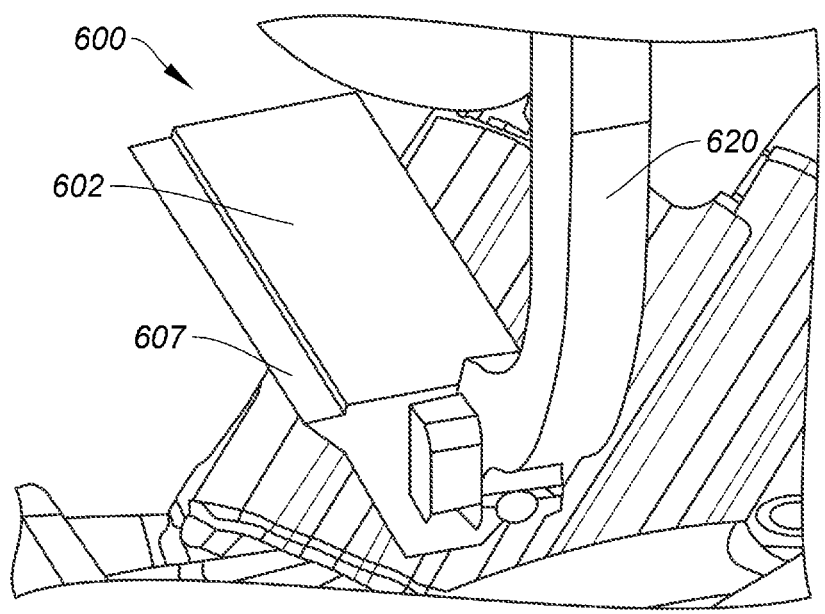

FIGS. 6A-6B illustrate a cartridge 600 according to some embodiments. FIG. 6A illustrates a side perspective view of cartridge 600 and FIG. 6B illustrates a top perspective view of cartridge 600.

Cartridge 600 may have a generally trapezoidal shape. Alternatively, cartridge 600 may have other shapes such as pyramidal or rectangular, as suitable to accommodate the probe device and/or subject animal of interest. Cartridge 600 may include a projected edge 607. Projected edge 607 may extend from an upper surface 602 of cartridge 600. Projected edge 607 can be configured to align the receiving features (e.g., 409 of FIG. 4) of the probes for engagement. Projected edge 607 may be similar to projected edge 705, described below with respect to FIG. 7.

As illustrated in FIG. 6A, a lower surface 603 of cartridge 600 may include one or more pillbox-cartridge engagement features 601. Pillbox-cartridge engagement features 601 may be configured to removably couple the cartridge 600 with a storage package structure of a probe device assembly, such as storage package structure 423 of FIG. 4 or storage package structure 506 of FIG. 5. Pillbox-cartridge engagement features 601 may engage with a reciprocal pillbox-cartridge engagement feature located on the storage package structure of the probe device assembly (e.g., 417 of FIG. 4). The pillbox-cartridge engagement feature 601 can include magnets, mechanical alignment elements, or a combination thereof. The lower surface 603 can have a shape configured to attach to a storage package structure of the probe device assembly, and can have projections, a latching mechanism, or a bracketing mechanism to mechanically couple with a storage package structure.

Cartridge 600 is shown attached to robotic arm 620. One or more side surfaces 605 of the cartridge 600 can include robotic arm engagement features that are configured to attach cartridge 600 to a robotic arm 620 of a surgical robot or the like. In some embodiments, cartridge 600 may include robotic arm engagement features on both side surfaces 605, shown as exposed on one side (unattached to a robotic arm) in FIG. 6A, and coupled to a robotic arm (and thus blocked from view) in FIG. 6B. Cartridge 600 may be configured to removably attach to robotic arm 620 via magnetic and/or mechanical attachment means.

Cartridge 600 may further include a temporary attachment surface for removable attachment of one or more probes. Such a temporary attachment surface is described in further detail below with respect to FIG. 7.

In some implementations of the systems and methods of the present disclosure, the shape and configuration of the cartridge used for inserting a probe device into neurological tissue is the same for both the left and right sides of a brain. In other implementations, two separate types of cartridges (often mirrored in shape and configuration) are used for inserting a probe device into neurological tissue is the same for the left and right sides of a brain, respectively.

Cartridge-Pillbox Assembly

FIG. 7 illustrates a cartridge-pillbox assembly 700 according to some embodiments. Cartridge-pillbox assembly 700 includes a cartridge 703, a storage package structure 701, and a plurality of probes 707.

Cartridge 703 may be substantially similar to cartridge 600, described above with respect to FIGS. 6A and 6B. Cartridge 703 may include engagement features for removable attachment to a robotic arm (as shown in FIG. 6; not pictured in FIG. 7).

Storage package structure 701 may be a structure for containing circuitry and/or organizing connections for a set of probes 707. Storage package structure 701 may be similar to storage package structure 423 of FIG. 4 and/or storage package structure 506 of FIG. 5. As described above with respect to FIG. 6, storage package structure 701 and cartridge 703 may be removably attached to one another, e.g., using magnetic and/or mechanical attachment means. In particular, Storage package structure 701 is shown with cartridge 703 mounted on a top surface of storage package structure 701.

Probes 707 may be wires dispersed with electrodes for implantation into biological tissue, as described above with respect to probes 421 FIGS. 4 and 504 of FIG. 5. Probes 707 may be removably coupled to cartridge 703. Probes 707 may be mounted on cartridge 703 in a position ready to be engaged with by an needle and implanted into biological tissue.

Cartridge 703 may include a projected edge 705 that extends a distance away from the main body of the cartridge. Probes 707 may extend out of storage package structure 701 and be arranged such that a receiving feature of each probe 707 is mounted on projected edge 705 so as to present a receiving feature 704 (e.g., a loop) of each probe 707 in an engageable position. In other words, an electrode-loaded filament-like wire is positioned on projected edge 705 of cartridge 703 such that a receiving feature 704 on an end of the wire can be engaged with by another structure, such as an needle.

Projected edge 705 may extend outward from an upper surface of cartridge 703 at an angle that is arranged to best present the receiving portions of each probe 707. In some implementations, projected edge 705 extends out at a 37° angle (relative to the upper surface of cartridge 303). In some aspects, projected edge 705 may extend out at an angle that is from about 270 to about 47° (relative to the upper surface of the cartridge).

FIG. 7 further illustrates a needle 710 that can be manipulated by a robotic arm system to reversibly engage with probe 707. In particular, a point of needle 710 can pass through receiving feature 704 of probe 707, where the angle and force of needle 710 as needle 710 passes through receiving feature 704 can pull probe 707 away from cartridge 703. In further aspects, needle 710 may include an engagement feature, such as a step, shelf, ledge, prong, or other such structure, that is configured to physically couple with (e.g. catch, hold, or secure) the receiving feature of probe 707. In implementation, needle 710 may serially engage with each probe 707, drive probe 707 in a direction (e.g., downward into tissue), and then disengage from probe 707 and retract back to a pre-engagement position. Through this process, a robotically controlled needle 710 can repeatedly, and in any sequence, engage with one or more probes 707 of a probe device assembly as mounted on projected edge 705 of cartridge 703.

In some embodiments, probes 707 are removably adhered or coupled to a temporary attachment surface. In this context, the term adhere can be used to indicate that the probes are loosely associated with the flexible backing sheet such that they can be removed from the flexible backing sheet by an engaged needle. The probes 707 can be adhered to the flexible backing sheet in such a way that they remain associated with the sheet in an organized manner (e.g., with regular spacing forming an array of probes 707) until a probe 707 is engaged with needle 710 and peeled (delaminated) from the flexible backing sheet. In other words, needle 710 may engage with and pull probe 707 with sufficient mechanical force to overcome the strength of the adhesion between probe 707 and the flexible backing sheet without disturbing other probes 707 which are still affixed to the backing sheet or already implanted in tissue. In such implementations, needle 710 can be moved to catch the receiving element of probe 707 and to move with a peeling motion to pull probe 707 off of the flexible backing sheet without damaging probe 707.

In some embodiments, probes 707 can adhere to the flexible backing sheet by way of being deposited on a thin film. The flexible backing sheet may be a flexible material that forms a thin film, such as parylene, a parylene-based polymer, and/or the like. Such a thin film may be attached to the cartridge via an adhesive layer. In some embodiments, the flexible backing sheet can include one or more dielectric layers to facilitate release of probes 707 from the flexible backing sheet (e.g., in proximity to the electrodes). In some embodiments, the flexible backing sheet can be bonded or adhered to a solid support (e.g., stainless steel such as magnetic stainless steel) that permits handling by a machine and/or human. As another example, probes 707 may be deposited on a silicon backing such that the probes can be peeled off of the silicon backing. The silicon backing may be bonded to a substrate such as a black glass slide. The substrate may be bonded (e.g., with an adhesive layer) to the cartridge. Alternatively, or additionally, an adhesive substance can be used to adhere the probes to the flexible backing sheet.

The organized adherence of probes 707 to the flexible backing sheet can enable the use of robotic surgery techniques. As discussed above, computer vision techniques can be used to guide needle 710 to engage with probe 707 and remove probe 707 from cartridge 703 in an organized fashion.

In some embodiments, a cartridge-pillbox assembly, includes (a) a plurality of probes that each have: (i) a biocompatible substrate (e.g., the wire 408 of FIG. 4); (ii) at least one electrode disposed on the biocompatible substrate; and (iii) a receiving feature configured for reversible engagement with a corresponding engagement feature of an needle, and (b) a flexible backing sheet to which the plurality of probes is adhered. The cartridge-pillbox assembly may further include a pillbox or storage package structure housing electronics and removably attached to the cartridge.

In some embodiments, the cartridge-pillbox assembly may be manufactured as a single unit. Upon implantation of the a probe device, the cartridge may be removed from cartridge arm 320 and replaced with a new cartridge-pillbox assembly.

Probe Selection and Manipulation

Figure 8A:
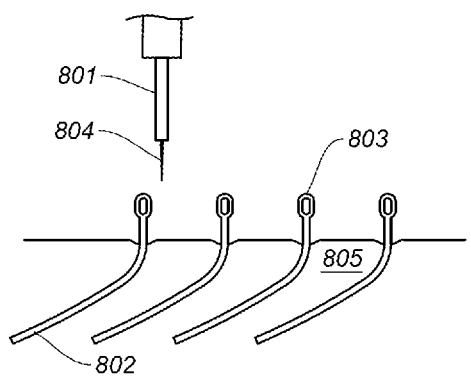
FIGS. 8A-8D illustrate selection and manipulation of a probe of a probe device assembly some aspects of the present disclosure.
Figure 8B:
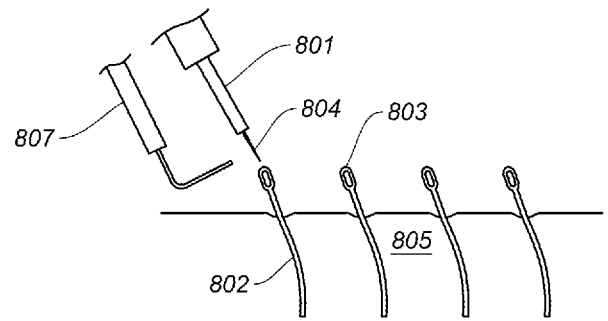
Figure 8C:
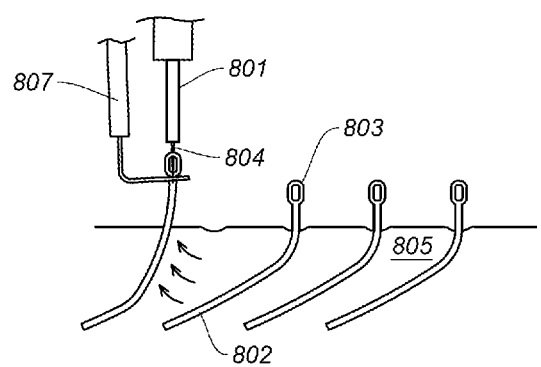
Figure 8D:
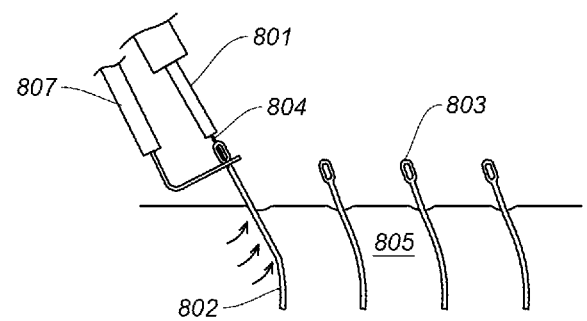

FIGS. 8A-8D illustrate engaging a needle with a probe and removing the probe from a cartridge. FIGS. 8A and 8B show two views of a needle assembly 801 preparing to engage with a probe 802. Probe 802 includes a receiving feature 803. Needle assembly 801 includes a needle 804 and a pincher 807. FIGS. 8C and 8D show two views of needle assembly 801 upon engagement with probe 802.

In FIGS. 8A and 8B, probes 802 are disposed on temporary attachment surface 805 (e.g., a thin film of parylene or silicon, as described above with respect to FIG. 7). Needle assembly 801 may be guided towards receiving feature 803. As described above with respect to FIG. 2, the needle assembly may be attached to an insertion arm (e.g., insertion arm 230) which may be coupled to a microprocessor controller that controls motion of the insertion arm and attached needle assembly. Given that the needle 804, receiving feature 803, and probe 802 may be on the micron scale, specialized computer vision techniques may be used to guide the needle 804 to engage with the probe 802 (e.g., using light pipe assemblies 306 and visualization devices 204, 206, 302, 304, as described above with respect to FIGS. 2 and 3). Such computer vision techniques are described in detail in the '520 application.

In FIGS. 8C and 8D, needle 804 on needle assembly 801 engages with receiving feature 803 of a selected probe 802. Needle 804 may hook onto the receiving feature 803 to reversibly engage needle 804 to the probe 802. Pincher 807 may pinch receiving feature 803 against needle 804 to secure probe 802 to needle 804. In order to pinch receiving feature 803 against needle 804, pincher 807 may rotate. In some embodiments, pincher 807 extends from needle assembly 801 as needle 801 is inserted into receiving feature 803.

When needle assembly 801 engages with probe 802 and moves upward, exerting an upward force on probe 802, probe 802 disengages from temporary attachment surface 805 and peels off of temporary attachment surface 805. At this point, a selected probe 802 is attached to needle 804, forming a loaded needle (i.e., a needle that is reversibly engaged with a receiving feature of a probe). At this point, the needle is loaded with the probe 802 and ready to implant probe 802 in a target such as biological tissue.

Implantation Methods

FIGS. 9A-9K illustrate example steps involved in a surgical process that implants probe devices such as those described herein. While the illustrated example is related to a neurosurgical process that implants probes of a probe device assembly in the brain, the systems and processes described herein can be used with any suitable biological tissue.

Figure 9A:
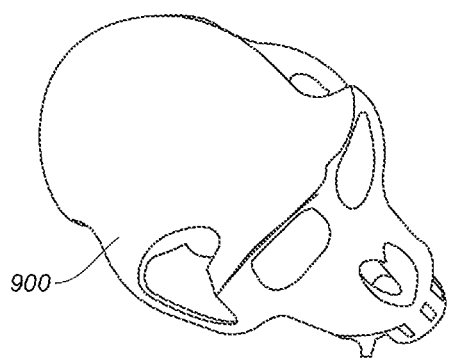
FIGS. 9A-9K illustrate a neurosurgical process, according to an aspect of the present disclosure.

FIG. 9A shows a skull 900. Skull 900 may initially be prepared for implantation. In some embodiments, a craniotomy may be performed prior to implantation, as shown in FIG. 9B. A craniotomy may be suitable for implantation of relatively large probe device assembly 400 shown in FIG. 4. Alternatively, to implant a smaller probe device assembly such as probe device assembly 500 shown in FIG. 5, one or more holes may be drilled into skull 900.

Figure 9B:
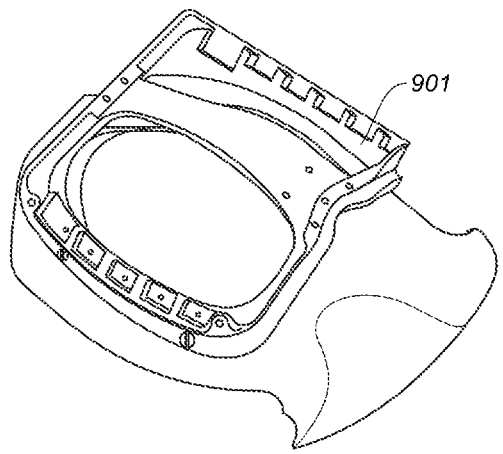

FIG. 9B shows a skull with a head plate 901 attached thereupon. As illustrated in FIG. 9B, a head plate 901 can be positioned on top of skull 900. In some embodiments, skull 900 can be mounted to a surgical stage (not shown). Head plate 901 can provide an organizational structure onto which probe device assemblies such as the one depicted in FIG. 4 can be attached. In some embodiments, the head plate 901 can be made of titanium or similar materials. Head plate 901 can be specially sized to the skull 900 using information obtained from computed tomography (CT) scans, magnetic resonance imaging (MRI) scans, and the like. Alternatively, to implant a smaller probe device as shown in FIG. 5, no head plate, or a much smaller head plate, may be implemented.

Figure 9C:
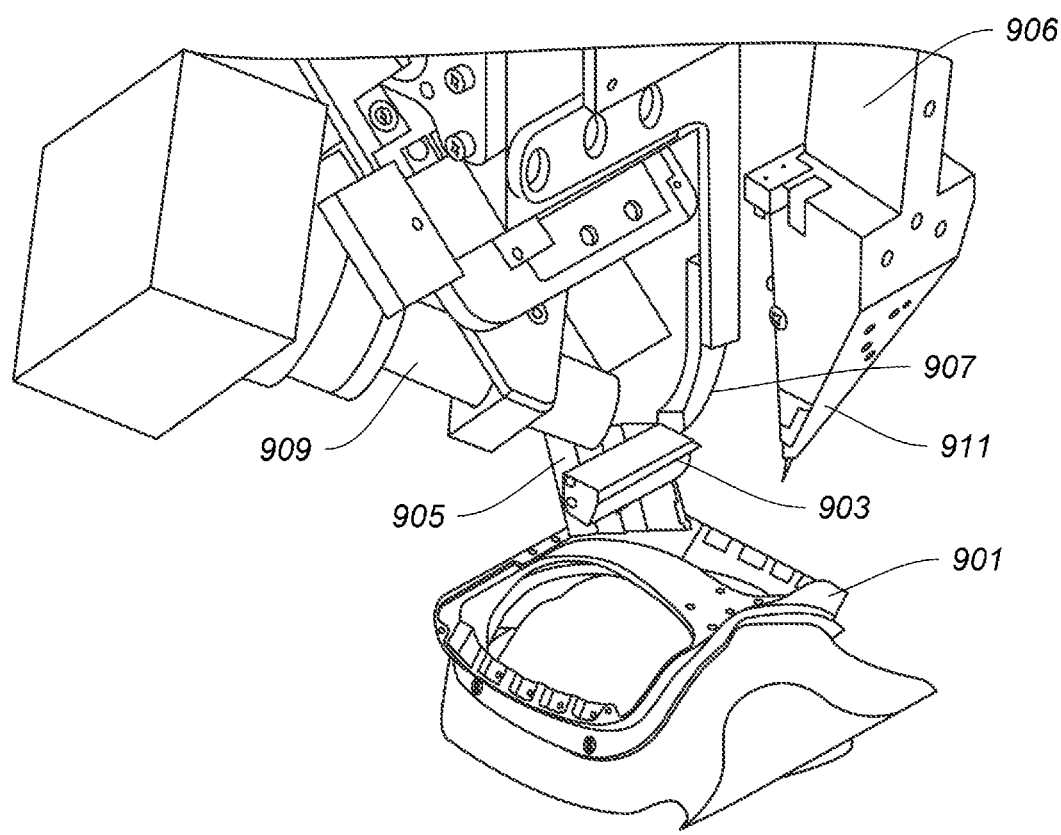

FIG. 9C illustrates an early stage of a neurosurgical process. A needle assembly 911 is guided to an initial position in proximity to a target implantation region. Needle assembly 911 may be mounted to and moved by a first robotic arm 906 (e.g. insertion arm 230 of FIG. 2). A cartridge 903 releasably coupled to probe device assembly 905 may also be guided to an initial position in proximity to the target implantation region. Cartridge 903 may be mounted to and moved by a second robotic arm 907 (e.g., cartridge arm 320 of FIG. 3). As described above with respect to FIGS. 2 and 3, motion of first robotic arm 906 and second robotic arm 907 may be controlled by separate respective microprocessor controllers and/or a shared microprocessor controller.

Figure 9D:
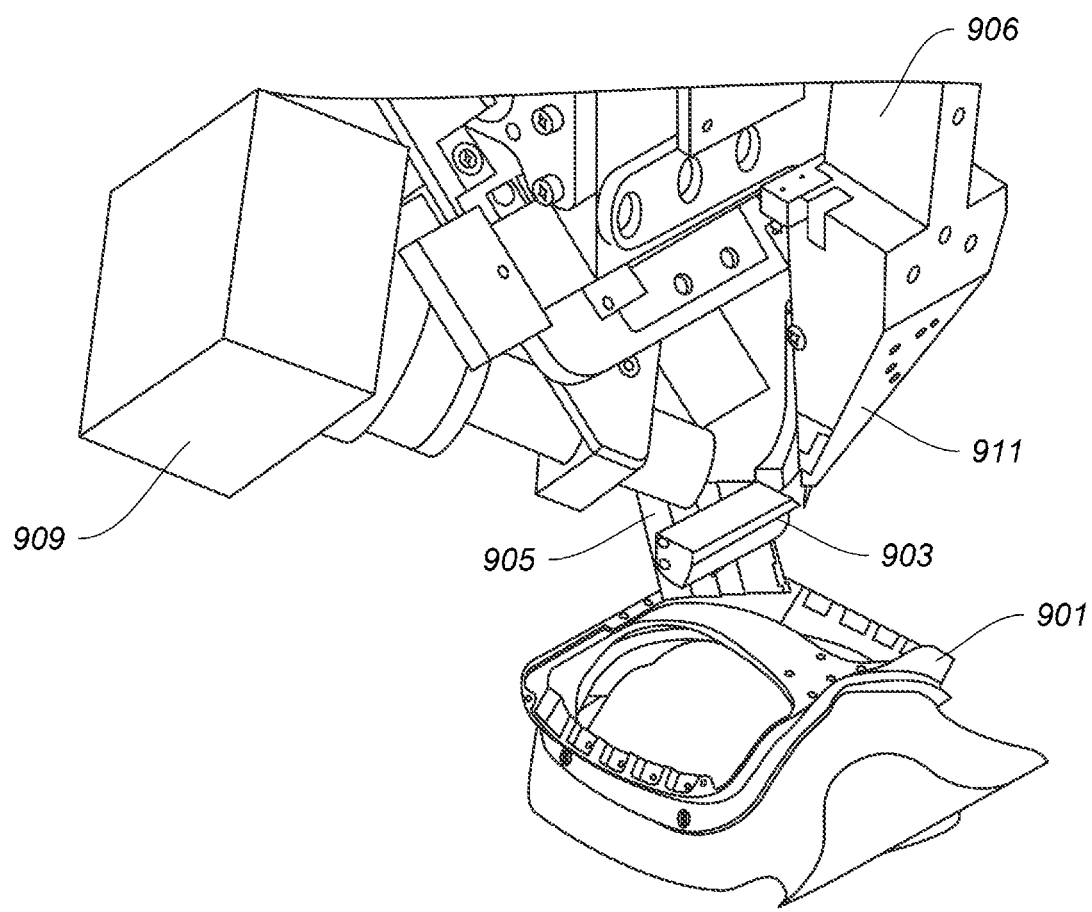

FIG. 9D illustrates the neurosurgical process at a second time when the first robotic arm and second robotic arm have moved to begin the implantation process. Probe device assembly 905 has been secured to head plate 901. This may be accomplished by mechanically latching or bracketing probe device assembly 905 on head plate 901. Robotic arms 906 and 907 can be guided at least in part by computer vision techniques involving visualization devices 909 (e.g., cameras, photodetectors, photomultiplier tubes, etc.).

As illustrated in FIG. 9D, the needle from the needle assembly 911 can engage with the receiving features of a probe located along the cartridge 903, implant the probe into the biological tissue (e.g., brain), and then disengage with the implanted probe. The process can be repeated, serially across cartridge 903 for all of the probes of a given probe device assembly 905, and sequentially for subsequent cartridges 903 coupled with subsequent probe device assemblies 905. In some embodiments, the probe can be driven one to two millimeters (1-3 mm) into the biological tissue. In this manner, the needle assembly 911 can be used to implant a set of probes having receiving features assembled on the cartridge 903. It should be understood that the receiving features of a probe can be considered as reciprocal engagement features to an engagement feature that is part of the structure of an needle.

In some embodiments, the implantation of the probe into the biological tissue can include the use of a "touch-down" sensor (described above with respect to FIG. 2). The touch-down sensor can be deployed from the needle assembly 911 and then retracted into the needle-pincher assembly when the presence of the biological tissue is detected. The needle can then be configured to implant the probe upon retraction of the touch-down sensor. The touch-down sensor can be retracted and the needle can implant the probe in less than approximately one tenth of a second (<0.1 sec). The touch-down sensor can be used for improved targeting along the Z-axis. Computer vision techniques (e.g., as described in the '520 application) can provide targeting along the X-axis and Y-axis of the target biological tissue.

Figure 9E:
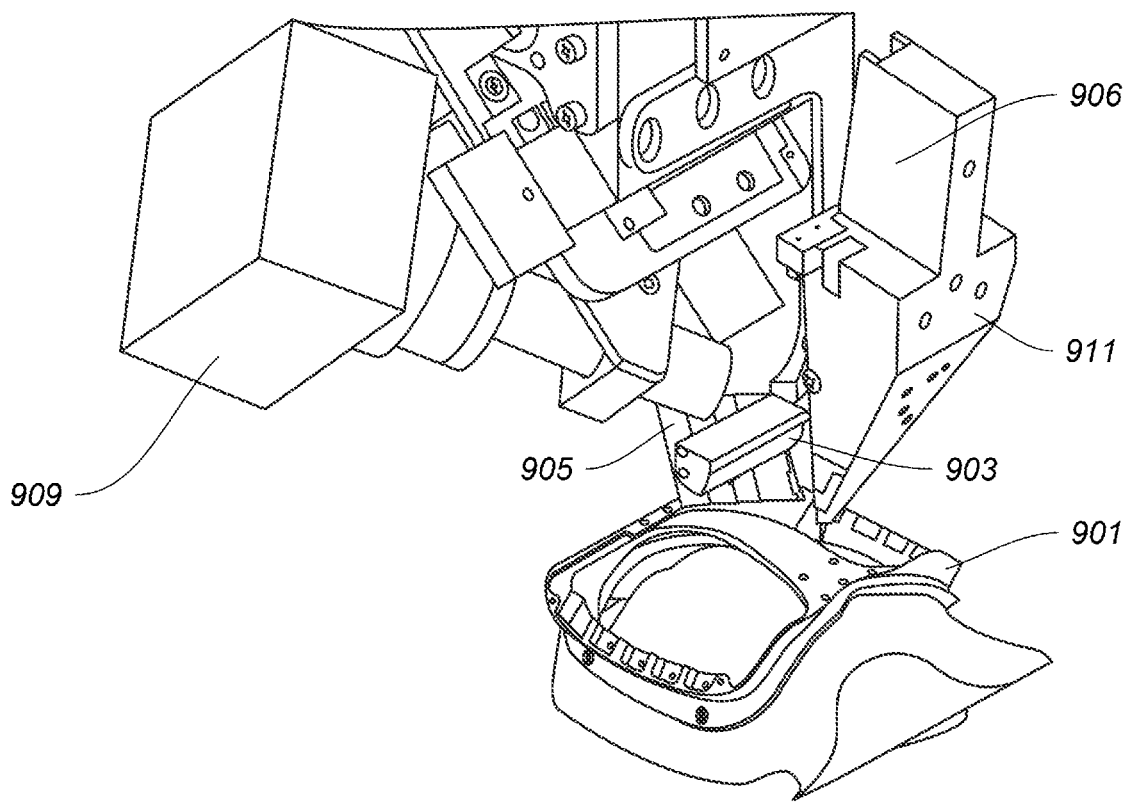

Once the probes from a pillbox-cartridge assembly are implanted in the biological tissue, needle assembly 911 can travel out of the area of the head plate 901 as is illustrated in FIG. 9E.

Figure 9F:
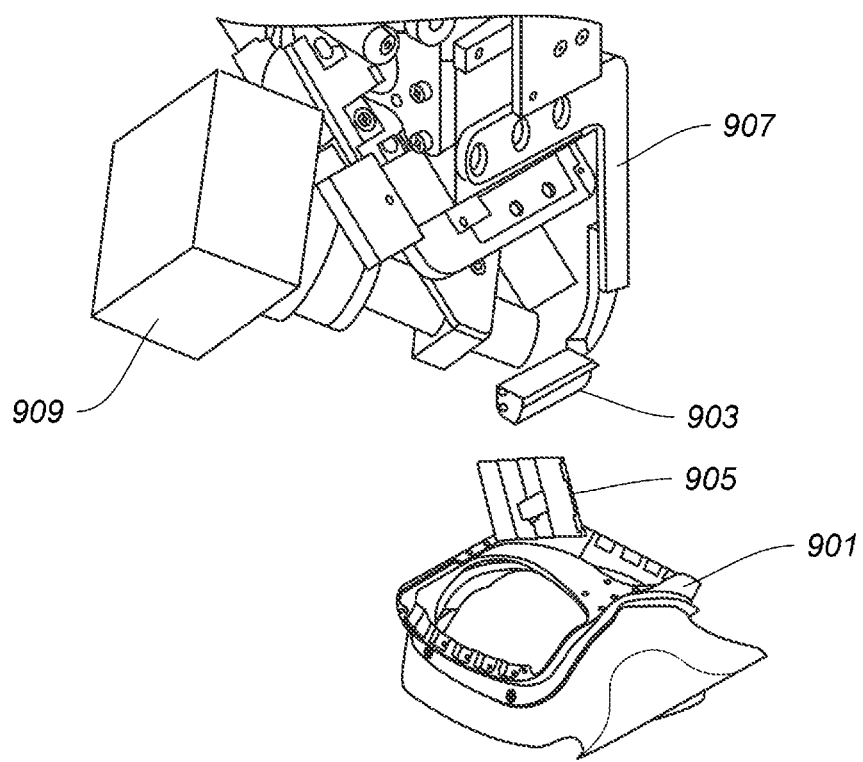

As illustrated in FIG. 9F, cartridge 903 can separate from probe device assembly 905. In some embodiments, the separation can involve releasing the magnetic hold between probe device assembly 905 and cartridge 903. In some such aspects, the magnetic hold can be released by lowering a surgical stage on which the biological tissue is placed. The physical distance between probe device assembly 905 and cartridge 903 may be increased until the magnetic attraction between probe device assembly 905 and cartridge 903 is not strong enough to retain their physical coupling. In other aspects, the magnetic hold can be released by lifting cartridge 903 vertically. In further embodiments, a combination of the two techniques can be used.

Figure 9G:
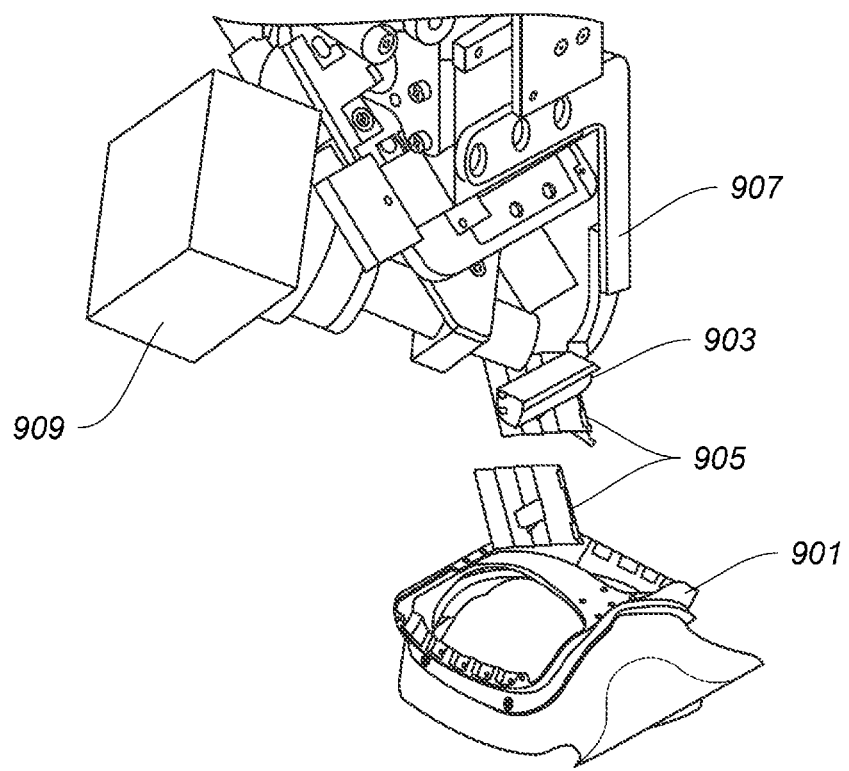

As illustrated in FIG. 9G, the process described above can be repeated with a subsequent cartridge-pillbox assembly, where a new cartridge-pillbox assembly is loaded onto the second robotic arm 907. After securing a first probe device assembly 905 to the head plate 901 and implanting the probe(s), the remaining cartridge 903 on the second robotic arm 907 can be removed, and then replaced with a new paired cartridge 903 and probe device assembly 905 set for the next implantation cycle. In some embodiments, one or more needles can be used to implant a plurality of probes coupled to one or more cartridges.

Figure 9H:
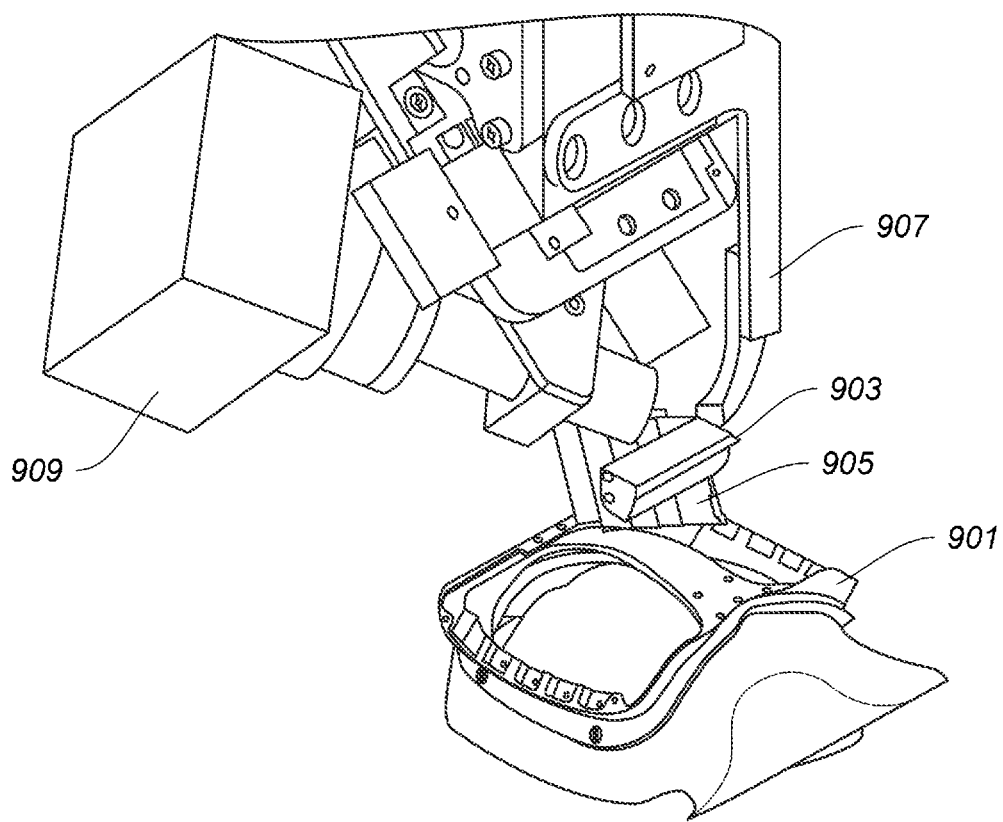
Figure 9I:
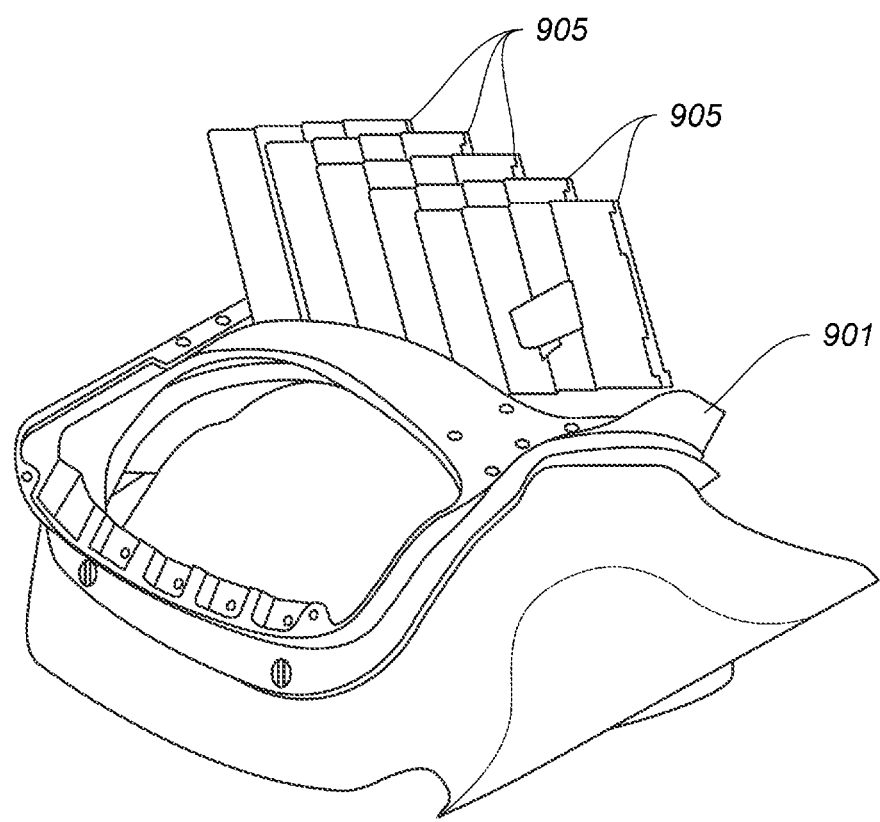

FIG. 9H illustrates a second probe device assembly 905 being positioned for implantation. FIG. 9I illustrates how a plurality of probe device assemblies 905 can appear once their respective probes are implanted.

Figure 9J:
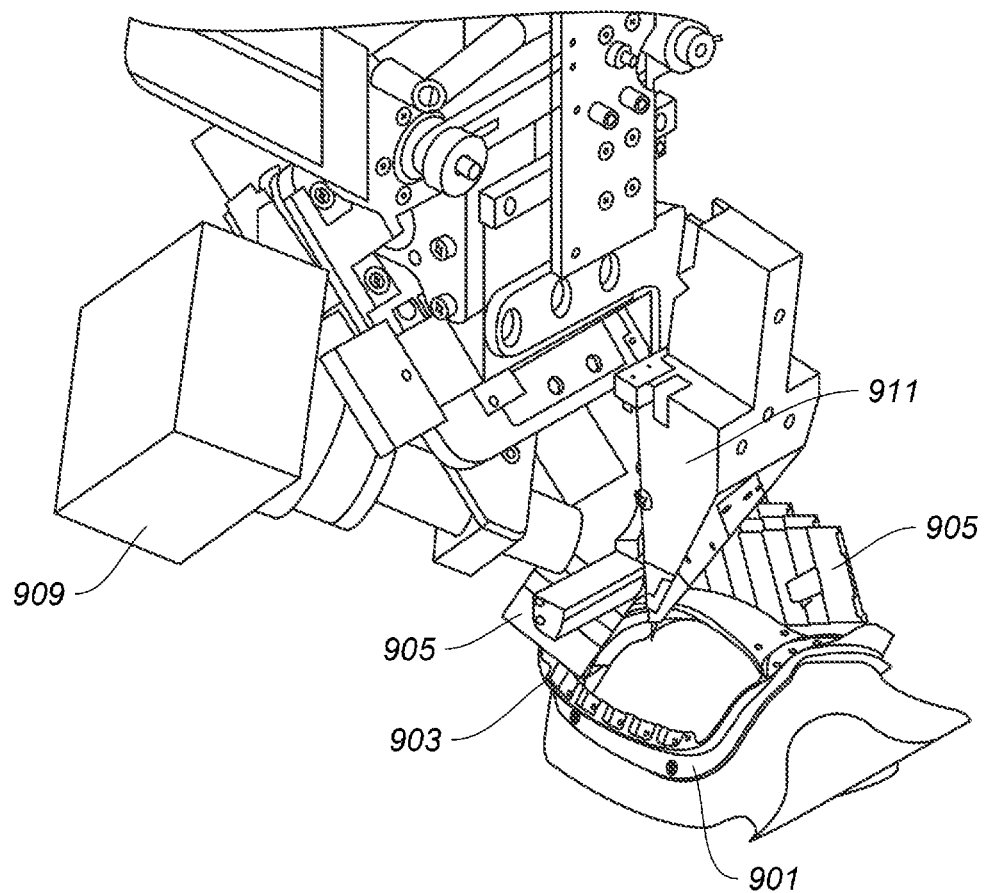
Figure 9K:
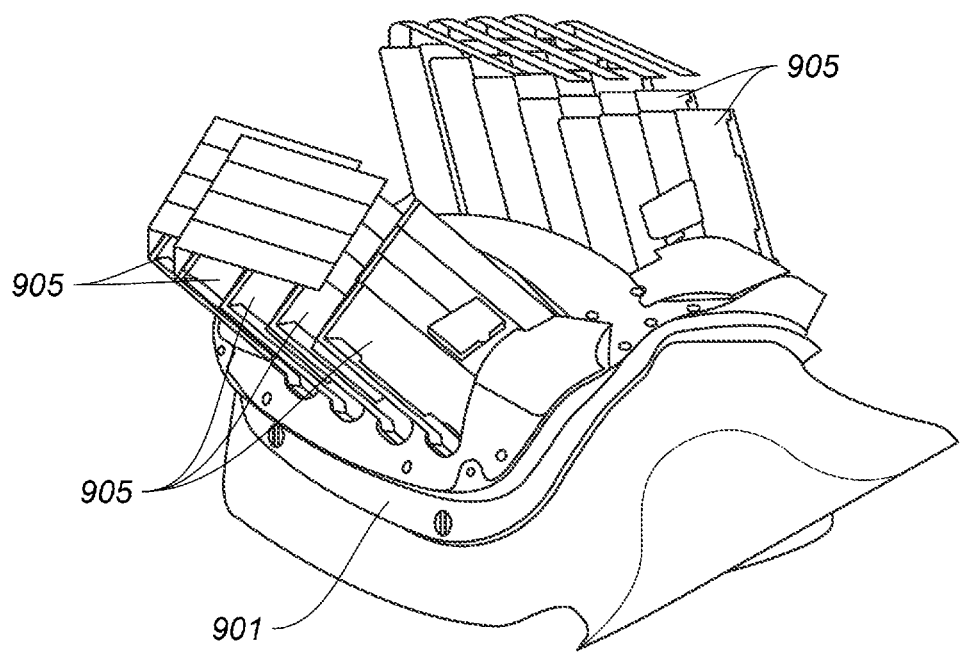

As illustrated in FIG. 9J, the process illustrated for the left hemisphere of the brain in FIGS. 9C-9I can be repeated on the right hemisphere of the brain. FIG. 9K illustrates how a plurality of probe device assemblies 905 can extend from the head plate once the probes are implanted in and on both sides of the brain.

Implanted Devices

Figure 10A:
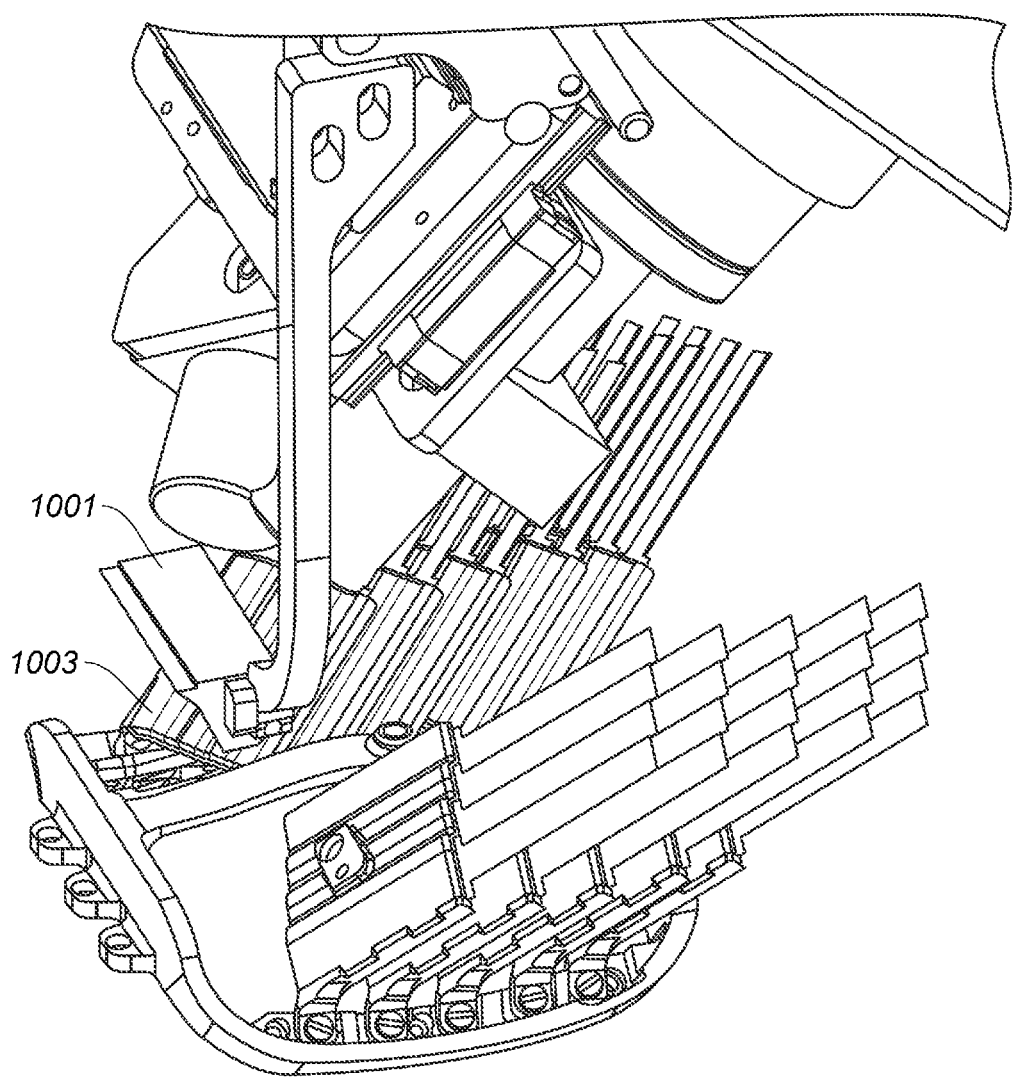
FIGS. 10A-10C illustrate implanted probe device assemblies, according to another aspect of the present disclosure.
Figure 10B:
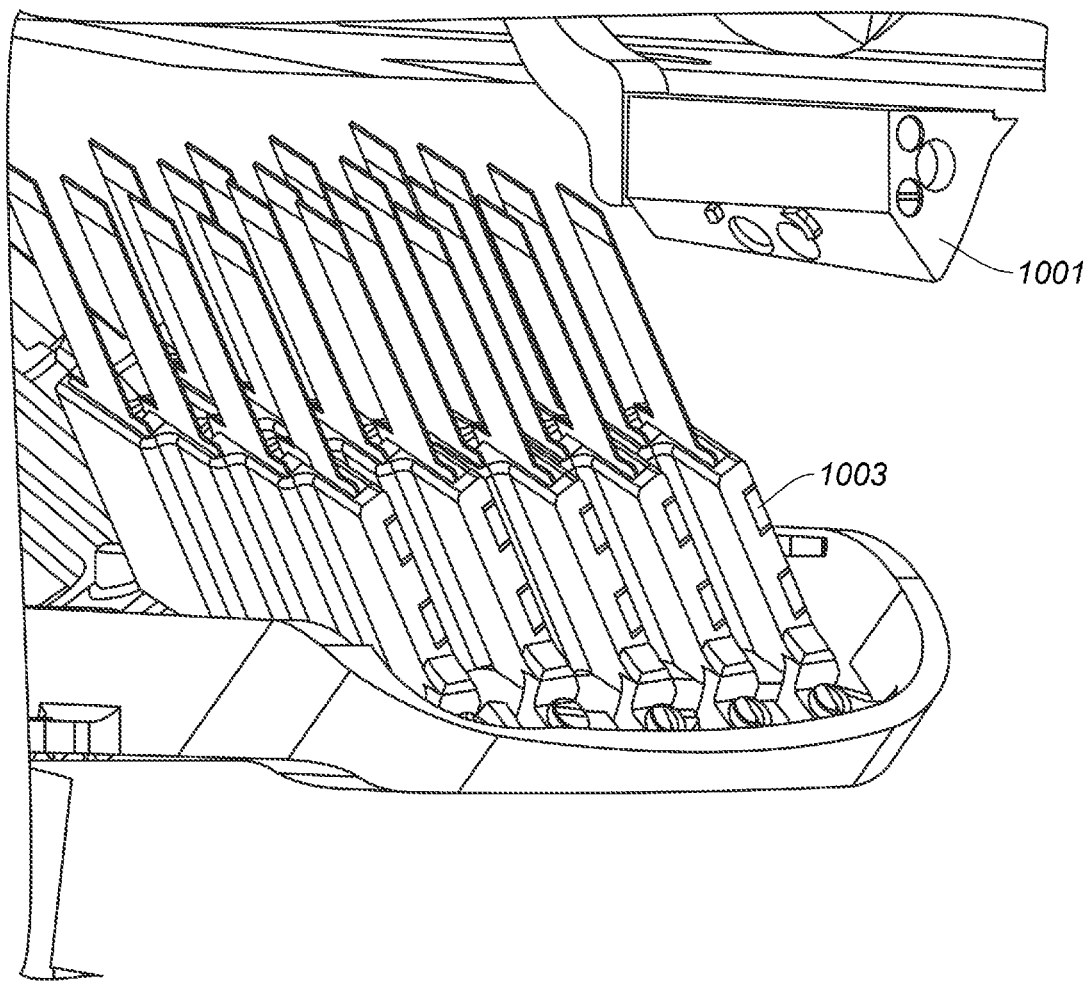
Figure 10C:
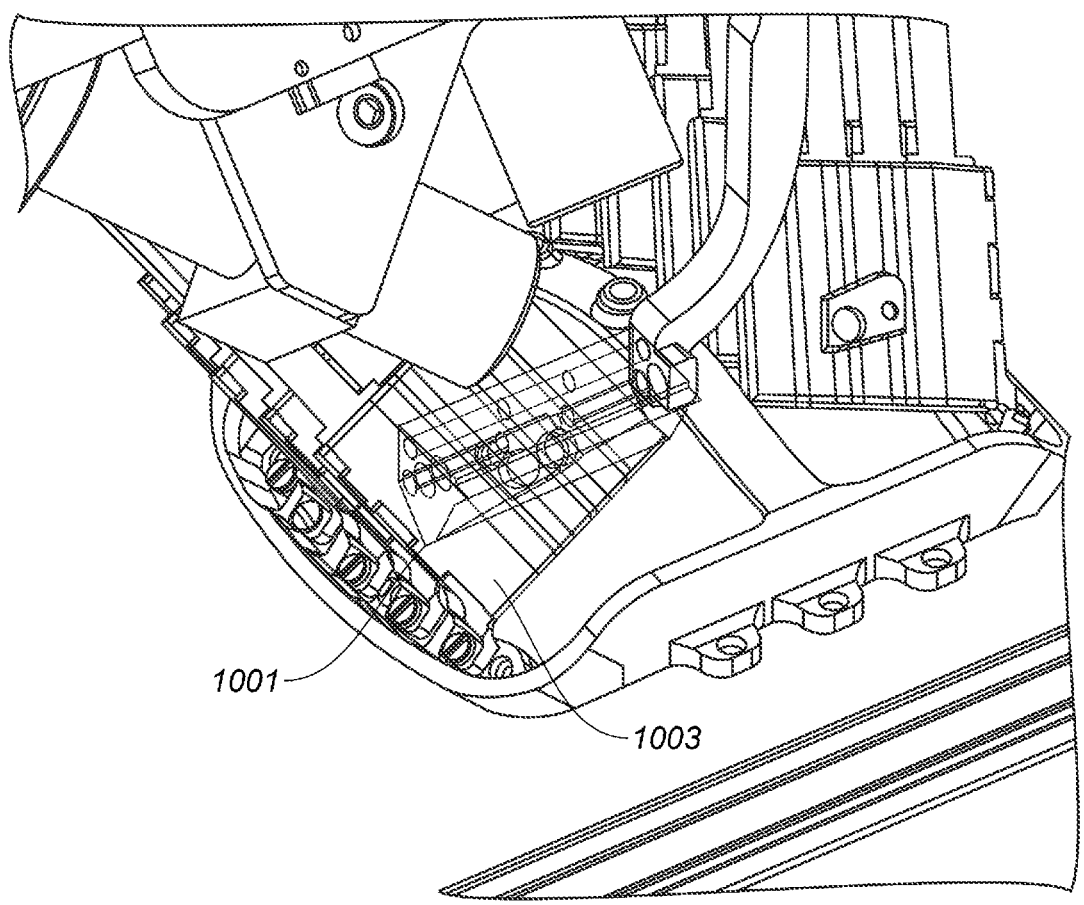

FIGS. 10A-10C illustrate implanted probe device assemblies 1003 according to some embodiments. FIG. 10A is a first view of a cartridge 1001 and probe device assemblies 1003 post-implantation. FIG. 10B is a second view of cartridge 1001 and probe device assemblies 1003 post-implantation, and FIG. 10C is a third view of cartridge 1001 and probe device assemblies 1003 post-implantation.

As shown in FIGS. 10A-10C, cartridge 1001 has disengaged from probe device assemblies 1003. The probes have been implanted in the biological tissue. This can be understood in accordance with the techniques discussed in connection with FIG. 9A-9K and FIG. 11. In particular, FIG. 10C represents the cartridge 1001 in a wireframe rendering to show the relative arrangement of the installed probe device assemblies 1003 beneath the cartridge 1001.

As pictured, each probe device assembly 1003, or a collection of probe device assemblies 1003, may include an antenna configured to relay data, electricity, or other signals. Alternatively, or additionally, probe device assemblies 1003 may be coupled to one or more cables leading out of the skull and skin of a subject (not pictured). A probe device assembly 1003, or a collection of probe device assemblies 1003, may include or be coupled to a communications port arranged to be exposed outside of the biological tissue and configured to relay data, electricity, or other signals. As an example, each probe device assembly 1003 may be coupled to a wire, and the wires may connect to lead out to a communications port (e.g., USB C cable) disposed outside of the skin and skull of the subject. In either case, the data may be relayed to a computing device for analyzing data gathered by the probe device assemblies 1003.

FIG. 11 illustrates implanted probe device assemblies according to other embodiments. The probe device assemblies of FIG. 11 may correspond to the probe device assembly 500 shown in and described above with respect to FIG. 5.

A plurality of storage package structures 1103 may be positioned on or above tissue proximate to the implantation area. For example, storage package structure 1103 may rest on the tissue or be affixed to the skull above the biological tissue implantation area. Accordingly, in some embodiments, the entire probe device assembly (e.g., storage package structure 1103 and one or more probes, which are not visible in FIG. 11) may be implanted below the skin of a subject. Storage package structures 1103 may hold one or more chips, and the chips may be coupled to probes implanted in the tissue (not pictured in FIG. 11).

The storage package structures 1103 may be coupled to respective connecting leads 1107. Connecting leads 1107 may, for example, be wires or flexible cable. Connecting leads 1107 may communicatively couple the storage package structures 1103 (e.g., the circuitry therein) to an internal hub 1105. Internal hub 1105 may gather data from each of the storage package structures 1103, as obtained via the respective probes thereof.

Internal hub 1105 may wirelessly communicate with an external hub 1109. In another embodiment, each probe device assembly may be in wireless communication with external hub 1109 (e.g., without internal hub 1105). External hub 1109 may process and/or store the received data. External hub 1109 may further transmit all or some of the received data to an external computing device with which external hub 1109 is in wired or wireless communication. For example, external hub 1109 may be coupled to an external computing device via a USB cable. Alternatively, or additionally, internal hub 1105 may be communicatively coupled to an external device via a wired connection.

In an example embodiment, which may correspond to the probe devices shown in any of FIGS. 10A-11, each probe may include approximately 1-100 electrodes configured to record and/or stimulate tissue. As many as 200 probes may be coupled to a storage package structure to form a probe device assembly. Approximately five probe device assemblies may be arranged on a hemisphere of a brain for a total of ten probe device assemblies. Accordingly, the arrangement can include tens of thousands of electrodes.

Implantation Flow

Figure 12:
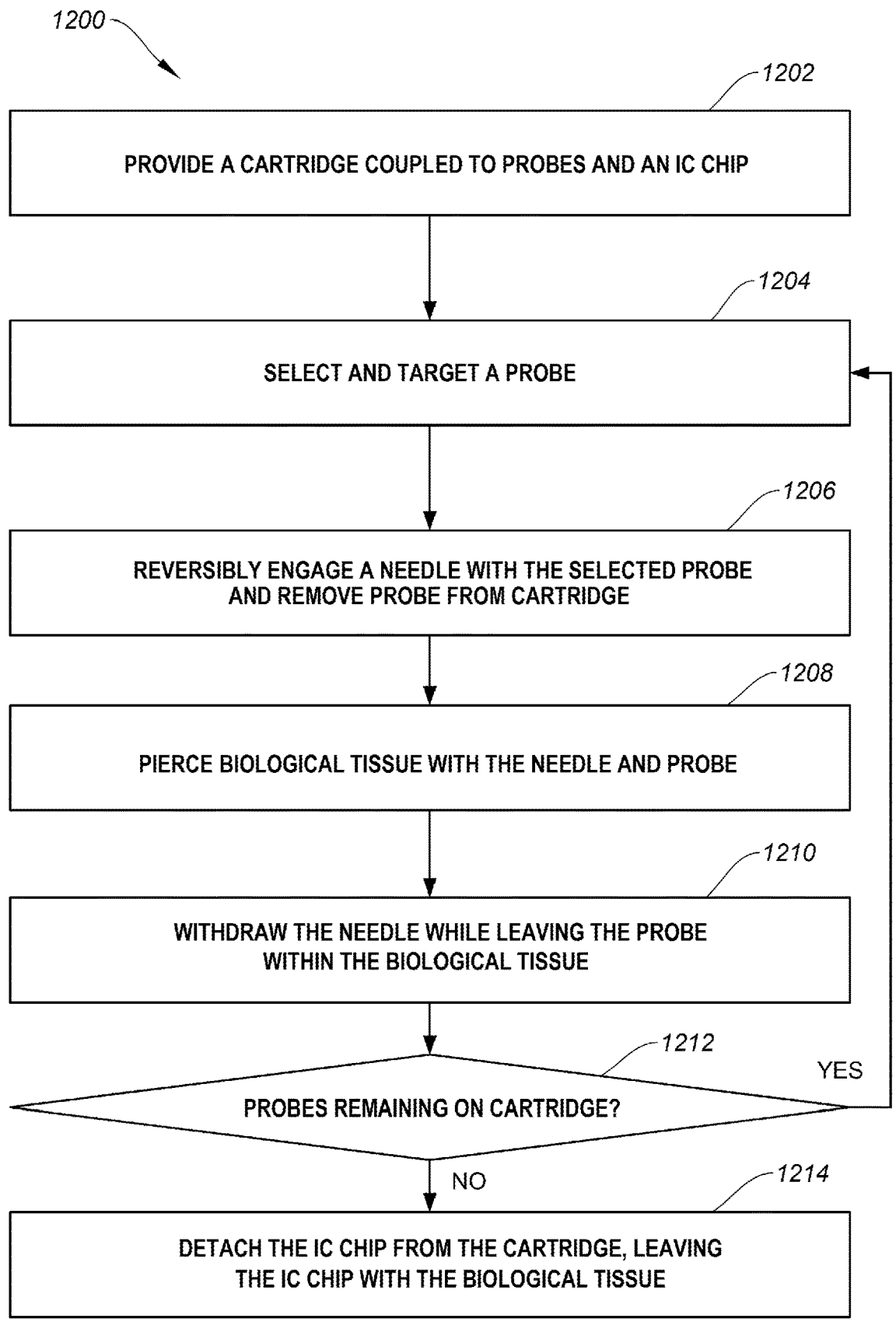
FIG. 12 is an example flowchart describing a method of implanting a probe device, according to aspects of the present disclosure.

FIG. 12 is a flowchart illustrating a method 1200 of implanting a probe device into biological tissue, with various steps, or portions thereof, represented in the disclosed flowchart blocks.

At block 1202, the method can begin with providing a cartridge that is removably coupled to probes and an IC chip (e.g., the cartridge-pillbox assembly of FIG. 7). The IC chip may be may tethered to one or more probes. The cartridge-pillbox assembly may be removably coupled to a robot arm (e.g., cartridge arm 320 of FIG. 3). In some embodiments, the storage package structure may be attached to a head plate and/or directly to a portion of a subject's body such as a skull.

At block 1204, the method can include selecting and targeting a probe. For example, as shown in FIG. 7, the cartridge-pillbox assembly 700 includes five probes 707, each having a respective receiving feature 704. The system may select a particular probe, of the plurality of probes. The system may target the selected probe for engagement. The system may align the needle with the receiving feature of the selected probe.

At block 1206, the method can include reversibly engaging a needle with the selected probe. The needle may be guided to the receiving feature of the selected probe. In some embodiments, computer vision techniques may be used to guide the needle to engagement, as described in the '520 patent. Visualization components such as cameras and light pipes can be used to identify position information and transmit such information to one or more microprocessor controllers. The microprocessor controller(s) may control motion of one or more robot arms (e.g., insertion arm 230 of FIG. 2 and/or cartridge arm 320 of FIG. 3) to move an engagement component of the needle towards the selected receiving feature. The system may move the one or more robot arms, in some embodiments using visualization components (e.g., a camera, lighting devices, and/or the like), to engage the needle with the selected receiving feature. As an example, an insertion arm and a cartridge arm may move in concert to engage the probe with the needle. As another example, an insertion arm may move to engage with a probe of a static cartridge-pillbox assembly.

An engagement feature (e.g., a hook or the like) of the needle may catch the receiving feature of the probe. In some aspects, the motion of the needle engaging with the receiving feature of the probe device can include a partial rotation of the needle that aids with both the insertion of the probe device into biological tissue and the withdrawal of the needle once the probe device portion has been secured within the biological tissue. More specifically, once the needle has engaged with the probe receiving feature, the robotic arm controlling the motion of the needle can rotate a predetermined amount, further securing the probe device on the engagement feature of the needle. In various aspects, this rotation of the needle can be from about five to about one hundred eighty degrees (5°-180°), or increments or gradients of rotation within that range. In some aspects, where the probe device is in part made from a wire or filament, this rotation can encourage, nudge, or guide a portion of the probe device to align that wire or filament alongside the needle.

The engagement of the needle and receiving feature may be aided using a pincher to guide the probe (e.g., pincher 22 of FIG. 2). A robot arm, such as insertion arm 230 of FIG. 2, may pull upwards to peel the probe off of the cartridge, as illustrated in FIGS. 8A-8D. needle At block 1208, the method can include piercing biological tissue with the needle and the probe. In some implementations, the target depth of probe insertion can be from about one to three millimeters (1-3 mm), or increments or gradients of depth within that range. The loaded needle may be inserted into the biological tissue by application of a downward force on the needle via the insertion arm.

At block 1210, the method can include withdrawing the needle while leaving the probe within the biological tissue. The needle may be retracted by exerting a substantially upward force on the needle via the insertion arm. In some embodiments, the needle may be retracted by a linear motor at a rapid acceleration (e.g., up to 30,000 mm/s) to encourage separation of the needle from the probe. Alternatively, or additionally, torque may be applied to encourage disengagement of the probe and needle (e.g., by twisting the needle).

At block 1212, there may be a determination whether additional probes are on the cartridge. For example, the cartridge may initially be coupled to five probes as shown in FIG. 7, or as many as 200 probes in other embodiments. The system may, for example, use computer vision techniques to identify the presence or absence of probes on the cartridge. If probes remain on the cartridge, then the method may return to block 1204 to implant the next probe. If probes no longer remain on the cartridge (e.g., all probes on the cartridge have been implanted in the biological tissue), then the process may proceed to block 1214.

At block 1214, the IC chip is detached from the cartridge, leaving the IC chip with the biological tissue. "With the biological tissue" may refer to being in contact with, or within about 7 mm of, the biological tissue. For example, the storage package structure may be coupled to a head plate such that the storage package structure is touching, or hovering slightly over, the brain tissue. Such an implantation scheme is illustrated, for example, in FIG. 10A. As another example, the storage package structure may be affixed to a skull in proximity to brain tissue, as illustrated in FIG. 11. The probes may extend from the storage package structure and into the brain tissue, with the storage package structure disposed thereupon to hold circuitry for gathering and analyzing information retrieved via the probes.

The cartridge may be disengaged from the storage package structure by applying an upward force on the cartridge and/or a downward force on the target tissue to overcome the magnetic attraction between the storage package structure and the cartridge. Disengagement of the storage package structure and cartridge is further described above with respect to FIG. 9F.

In some embodiments, additional probe device assemblies may be implanted by repeating steps 1202-1214. This may result in the implantation of multiple probe devices. For example, in FIG. 10A, ten probe device assemblies have been implanted, and in FIG. 11, four probe device assemblies have been implanted. In some aspects, when implanting a device into a brain, the next cartridge can be on the same brain hemisphere side as the previous installed cartridge, or on the opposite brain hemisphere side.

The systems and methods described herein may be capable of inserting about six probes per minute. For example, with 32 electrodes per probe, the system can insert up to 192 electrodes per minute. Further, the needle assembly can be replaced mid-surgery in under a minute. Accordingly, the techniques described herein enable rapid implantation of hundreds or up to tens of thousands of electrodes in biological tissue.

The probe devices described herein can be used for science and research experiments, neural prostheses (e.g., brain/nerve machine interfaces) and the treatment of neuronal disease (e.g., deep brain stimulation for the treatment of epilepsy, sensory recording and/or electrical stimulation for the treatment of Alzheimer's disease, sensory recording and/or electrical stimulation for the treatment of Parkinson's disease, or the like).

In some embodiments, the probe device can be configured for implantation in biological tissue. Biological tissue may include, but is not limited to, the brain, muscle, liver, pancreas, spleen, kidney, bladder, intestine, heart, stomach, skin, colon and the like. Additionally, the electrode array designs may be used in connection with any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue may be ex vivo (e.g., tissue explant), or in vivo (e.g., the method is a surgical procedure performed on a patient).

Example Computer System

Figure 13:
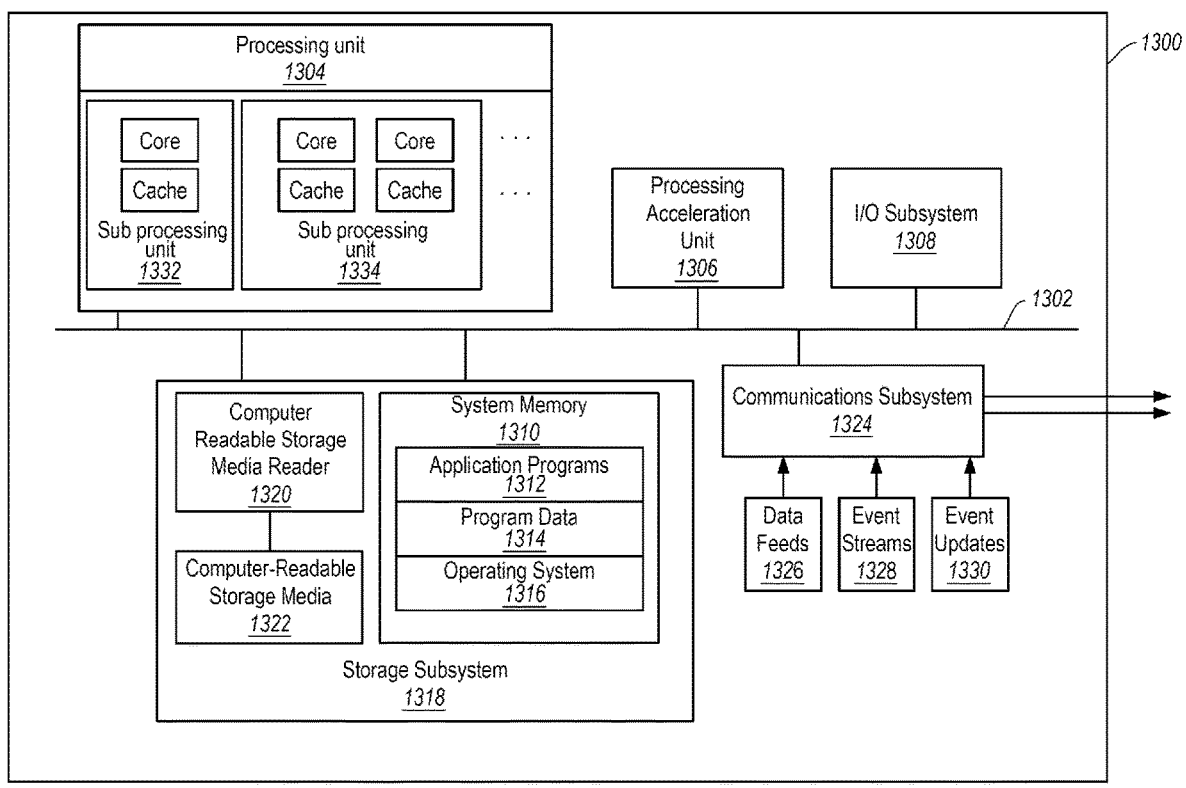
FIG. 13 illustrates an example computer system that may be used to implement certain embodiments.

FIG. 13 illustrates an example computer system 1300 that may be used to implement certain embodiments. For example, in some embodiments, computer system 1300 may be used to implement any of the systems for robotically implanting a probe device into biological tissue described above. As shown in FIG. 13, computer system 1300 includes various subsystems including a processing subsystem 1304 that communicates with a number of other subsystems via a bus subsystem 1302. These other subsystems may include a processing acceleration unit 1306, an I/O subsystem 1308, a storage subsystem 1318, and a communications subsystem 1324. Storage subsystem 1318 may include non-transitory computer-readable storage media including storage media 1322 and a system memory 1310.

Bus subsystem 1302 provides a mechanism for letting the various components and subsystems of computer system 1300 communicate with each other as intended. Although bus subsystem 1302 is shown schematically as a single bus, alternative embodiments of the bus subsystem may utilize multiple buses. Bus subsystem 1302 may be any of several types of bus structures including a memory bus or memory controller, a peripheral bus, a local bus using any of a variety of bus architectures, and the like. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard, and the like.

Processing subsystem 1304 controls the operation of computer system 1300 and may comprise one or more processors, application specific integrated circuits (ASICs), or field programmable gate arrays (FPGAs). The processors may include be single core or multicore processors. The processing resources of computer system 1300 can be organized into one or more processing units 1332, 1334, etc. A processing unit may include one or more processors, one or more cores from the same or different processors, a combination of cores and processors, or other combinations of cores and processors. In some embodiments, processing subsystem 1304 can include one or more special purpose co-processors such as graphics processors, digital signal processors (DSPs), or the like. In some embodiments, some or all of the processing units of processing subsystem 1304 can be implemented using customized circuits, such as application specific integrated circuits (ASICs), or field programmable gate arrays (FPGAs).

In some embodiments, the processing units in processing subsystem 1304 can execute instructions stored in system memory 1310 or on computer readable storage media 1322. In various embodiments, the processing units can execute a variety of programs or code instructions and can maintain multiple concurrently executing programs or processes. At any given time, some or all of the program code to be executed can be resident in system memory 1310 and/or on computer-readable storage media 1322 including potentially on one or more storage devices. Through suitable programming, processing subsystem 1304 can provide various functionalities described above. In instances where computer system 1300 is executing one or more virtual machines, one or more processing units may be allocated to each virtual machine.

In certain embodiments, a processing acceleration unit 1306 may optionally be provided for performing customized processing or for off-loading some of the processing performed by processing subsystem 1304 so as to accelerate the overall processing performed by computer system 1300.

I/O subsystem 1308 may include devices and mechanisms for inputting information to computer system 1300 and/or for outputting information from or via computer system 1300. In general, use of the term input device is intended to include all possible types of devices and mechanisms for inputting information to computer system 1300. User interface input devices may include, for example, a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may also include motion sensing and/or gesture recognition devices such as the Microsoft Kinect® motion sensor that enables users to control and interact with an input device, the Microsoft Xbox® 360 game controller, devices that provide an interface for receiving input using gestures and spoken commands. User interface input devices may also include eye gesture recognition devices such as the Google Glass® blink detector that detects eye activity (e.g., "blinking" while taking pictures and/or making a menu selection) from users and transforms the eye gestures as inputs to an input device (e.g., Google Glass®). Additionally, user interface input devices may include voice recognition sensing devices that enable users to interact with voice recognition systems (e.g., Siri® navigator) through voice commands.

Other examples of user interface input devices include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, and medical ultrasonography devices. User interface input devices may also include, for example, audio input devices such as MIDI keyboards, digital musical instruments and the like.

In general, use of the term output device is intended to include all possible types of devices and mechanisms for outputting information from computer system 1300 to a user or other computer. User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. For example, user interface output devices may include, without limitation, a variety of display devices that visually convey text, graphics and audio/video information such as monitors, printers, speakers, headphones, automotive navigation systems, plotters, voice output devices, and modems.

Storage subsystem 1318 provides a repository or data store for storing information and data that is used by computer system 1300. Storage subsystem 1318 provides a tangible non-transitory computer-readable storage medium for storing the basic programming and data constructs that provide the functionality of some embodiments. Storage subsystem 1318 may store software (e.g., programs, code modules, instructions) that when executed by processing subsystem 1304 provides the functionality described above. The software may be executed by one or more processing units of processing subsystem 1304. Storage subsystem 1318 may also provide a repository for storing data used in accordance with the teachings of this disclosure.

Storage subsystem 1318 may include one or more non-transitory memory devices, including volatile and non-volatile memory devices. As shown in FIG. 13, storage subsystem 1318 includes a system memory 1310 and a computer-readable storage media 1322. System memory 1310 may include a number of memories including a volatile main random access memory (RAM) for storage of instructions and data during program execution and a non-volatile read only memory (ROM) or flash memory in which fixed instructions are stored. In some implementations, a basic input/output system (BIOS), containing the basic routines that help to transfer information between elements within computer system 1300, such as during start-up, may typically be stored in the ROM. The RAM typically contains data and/or program modules that are presently being operated and executed by processing subsystem 1304. In some implementations, system memory 1310 may include multiple different types of memory, such as static random access memory (SRAM), dynamic random access memory (DRAM), and the like.

By way of example, and not limitation, as depicted in FIG. 13, system memory 1310 may load application programs 1312 that are being executed, which may include various applications such as Web browsers, mid-tier applications, relational database management systems (RDBMS), etc., program data 1314, and an operating system 1316. By way of example, operating system 1316 may include various versions of Microsoft Windows®, Apple Macintosh©, and/or Linux operating systems, a variety of commercially-available UNIX® or UNIX-like operating systems (including without limitation the variety of GNU/Linux operating systems, the Google Chrome© OS, and the like) and/or mobile operating systems such as iOS, Windows© Phone, Android© OS, BlackBerry® OS, Palm® OS operating systems, and others.

Computer-readable storage media 1322 may store programming and data constructs that provide the functionality of some embodiments. Computer-readable media 1322 may provide storage of computer-readable instructions, data structures, program modules, and other data for computer system 1300. Software (programs, code modules, instructions) that, when executed by processing subsystem 1304 provides the functionality described above, may be stored in storage subsystem 1318. By way of example, computer-readable storage media 1322 may include non-volatile memory such as a hard disk drive, a magnetic disk drive, an optical disk drive such as a CD ROM, DVD, a Blu-Ray© disk, or other optical media. Computer-readable storage media 1322 may include, but is not limited to, Zip® drives, flash memory cards, universal serial bus (USB) flash drives, secure digital (SD) cards, DVD disks, digital video tape, and the like. Computer-readable storage media 1322 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs.

In certain embodiments, storage subsystem 1318 may also include a computer-readable storage media reader 1320 that can further be connected to computer-readable storage media 1322. Reader 1320 may receive and be configured to read data from a memory device such as a disk, a flash drive, etc.

In certain embodiments, computer system 1300 may support virtualization technologies, including but not limited to virtualization of processing and memory resources. For example, computer system 1300 may provide support for executing one or more virtual machines. In certain embodiments, computer system 1300 may execute a program such as a hypervisor that facilitated the configuring and managing of the virtual machines. Each virtual machine may be allocated memory, compute (e.g., processors, cores), I/O, and networking resources. Each virtual machine generally runs independently of the other virtual machines. A virtual machine typically runs its own operating system, which may be the same as or different from the operating systems executed by other virtual machines executed by computer system 1300. Accordingly, multiple operating systems may potentially be run concurrently by computer system 1300.

Communications subsystem 1324 provides an interface to other computer systems and networks. Communications subsystem 1324 serves as an interface for receiving data from and transmitting data to other systems from computer system 1300. For example, communications subsystem 1324 may enable computer system 1300 to establish a communication channel to one or more client devices via the Internet for receiving and sending information from and to the client devices. For example, the communication subsystem may be used to receive speech input from a client device and send a value to the client device in response.

Communication subsystem 1324 may support both wired and/or wireless communication protocols. For example, in certain embodiments, communications subsystem 1324 may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.XX family standards, or other mobile communication technologies, or any combination thereof), global positioning system (GPS) receiver components, and/or other components. In some embodiments communications subsystem 1324 can provide wired network connectivity (e.g., Ethernet) in addition to or instead of a wireless interface.

Communication subsystem 1324 can receive and transmit data in various forms. For example, in some embodiments, in addition to other forms, communications subsystem 1324 may receive input communications in the form of structured and/or unstructured data feeds 1326, event streams 1328, event updates 1330, and the like. For example, communications subsystem 1324 may be configured to receive (or send) data feeds 1326 in real-time from users of social media networks and/or other communication services such as Twitter® feeds, Facebook© updates, web feeds such as Rich Site Summary (RSS) feeds, and/or real-time updates from one or more third party information sources.

In certain embodiments, communications subsystem 1324 may be configured to receive data in the form of continuous data streams, which may include event streams 1328 of real-time events and/or event updates 1330, that may be continuous or unbounded in nature with no explicit end. Examples of applications that generate continuous data may include, for example, sensor data applications, financial tickers, network performance measuring tools (e.g. network monitoring and traffic management applications), clickstream analysis tools, automobile traffic monitoring, and the like.

Communications subsystem 1324 may also be configured to communicate data from computer system 1300 to other computer systems or networks. The data may be communicated in various different forms such as structured and/or unstructured data feeds 1326, event streams 1328, event updates 1330, and the like to one or more databases that may be in communication with one or more streaming data source computers coupled to computer system 1300.

Computer system 1300 can be one of various types, including a handheld portable device (e.g., an iPhone® cellular phone, an iPad® computing tablet, a PDA), a wearable device (e.g., a Google Glass® head mounted display), a personal computer, a workstation, a mainframe, a kiosk, a server rack, or any other data processing system.

Due to the ever-changing nature of computers and networks, the description of computer system 1300 depicted in FIG. 13 is intended only as a specific example. Many other configurations having more or fewer components than the system depicted in FIG. 13 are possible. Based on the disclosure and teachings provided herein, a person of ordinary skill in the art will appreciate other ways and/or methods to implement the various embodiments.

It should be appreciated that the robotic system handling, coupling with, and engaging with one or more portions of a probe device can include a control system (or microprocessor controller) having one or more microprocessors/processing devices that can further be a component of the overall system. The control system can be local or remote to the robotic system, and can also include a display interface and/or operational controls configured to be handled by a user to alter the program of the robotic arm, to visualize the probe device, to visualize biological tissue into which the probe device is being inserted, and change configurations of the robotic device, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++,C #, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A system for robotically implanting a probe device into biological tissue, comprising:
   a biocompatible probe;
   an integrated circuit (IC) chip tethered to the probe;
   a cartridge comprising a temporary attachment surface by which the probe is removably coupled to the cartridge;
   a needle configured to reversibly engage with the probe, wherein reversibly engaging the needle with the probe comprises rotating the needle and passing a point of the needle through a receiving feature of the probe;
   a robotic arm configured to hold the needle;
   a microprocessor controller configured to control the robotic arm and the needle in order to:
   remove the probe from the temporary attachment surface using the needle;
   pierce the biological tissue with the needle and the probe;
   withdraw the needle while leaving the probe within the biological tissue; and
   detach the IC chip from the cartridge and leave the IC chip with the biological tissue.

2. The system of claim 1, wherein:
   the cartridge has multiple probes and IC chips.

3. The system of claim 1, the cartridge further comprising a fastener comprising one or more of a magnetic attachment or a mechanical attachment.

4. The system of claim 1, wherein:
   the temporary attachment surface is formed of one or more of parylene or silicon; and
   the cartridge further comprises an adhesive layer beneath the temporary attachment surface.

5. The system of claim 1, wherein the probe further comprises:
   an electrode configured to be inserted into biological tissue.

6. The system of claim 1, wherein the robotic arm is a first robotic arm, further comprising:
   a second robotic arm configured to couple with the cartridge.

7. The system of claim 1, wherein the needle is rotated from about 5 degrees to about 180 degrees.

8. A method of implanting a probe device into biological tissue, comprising:
(i) providing a cartridge comprising a temporary attachment surface by which the cartridge is removably coupled to a biocompatible probe and a fastener by which the cartridge is removably coupled to an integrated circuit (IC) chip tethered to the probe;
(ii) reversibly engaging a needle with the probe, wherein reversibly engaging the needle with the probe comprises rotating the needle and passing a point of the needle through a receiving feature of the probe;
(iii) removing the probe from the temporary attachment surface using the needle;
(iv) piercing the biological tissue with the needle and the probe;
(v) withdrawing the needle while leaving the probe within the biological tissue; and
(vi) detaching the IC chip from the cartridge, leaving the IC chip with the biological tissue.

9. The method of claim 8, wherein:
the cartridge has multiple probes and IC chips; and
the method further comprises repeating steps (ii)-(v) for each probe, of the multiple probes.

10. The method of claim 8, wherein the needle is rotated from about 5 degrees to about 180 degrees.

11. The method of claim 8, wherein the probe is left within the biological tissue at a depth of about one to about three millimeters.

12. A cartridge-and-probe-device assembly comprising:
a cartridge comprising:
a first fastener;
a second fastener configured to removably couple the cartridge to a robotic arm;
a biocompatible probe configured to be engaged with by a needle for implementation, wherein engaging the needle with the probe comprises rotating the needle and passing a point of the needle through a receiving feature of the probe;
an integrated circuit (IC) chip removably coupled to the cartridge via the first fastener; and
the biocompatible probe tethered to the IC chip and removably coupled to the cartridge, wherein the probe includes an electrode configured to be inserted into biological tissue.

13. The cartridge-and-probe-device assembly of claim 12, further comprising a communications port arranged to be exposed outside of the biological tissue and configured to relay data, electricity, or other signals.

14. The cartridge-and-probe-device assembly of claim 12, wherein the first fastener comprises one or more of a magnetic attachment or a mechanical attachment.

15. The cartridge-and-probe-device assembly of claim 12, wherein the second fastener comprises one or more of magnetic attachment or mechanical attachment.

16. The cartridge-and-probe-device assembly of claim 12, further comprising:
multiple probes and IC chips,
wherein the cartridge is configured to mount the multiple probes in a position to be engaged with by the needle for implantation.

17. The cartridge-and-probe-device assembly of claim 12, further comprising:
four integrated circuit chips; and
a storage package structure comprising four chip-compartments, each chip-compartment holding a respective IC chip.

18. The cartridge-and-probe-device assembly of claim 12, the cartridge further comprising:
a temporary attachment surface formed of one or more of parylene or silicon; and
an adhesive layer below the temporary attachment surface.

19. The cartridge-and-probe-device assembly of claim 12, the probe having a thickness in a range of from about 2 micrometers ($\mu$m) to about 50 $\mu$m.

20. The cartridge-and-probe-device assembly of claim 12, wherein the needle is rotated from about 5 degrees to about 180 degrees.

* * * * *